(12) United States Patent
Gill et al.

(10) Patent No.: US 8,105,776 B2
(45) Date of Patent: Jan. 31, 2012

(54) BREED-SPECIFIC HAPLOTYPES FOR POLLED PHENOTYPES IN CATTLE

(75) Inventors: Clare A. Gill, Bryan, TX (US); Stewart Bauck, Cumming, GA (US); Brent Woodward, Lawrenceville, GA (US); Nathan Voss, Lawrenceville, GA (US)

(73) Assignees: Merial Limited, Duluth, GA (US); The Texas A&M University System, College Station, TX (US)

( * ) Notice: Subject to any disclaimer, the term of this patent is extended or adjusted under 35 U.S.C. 154(b) by 254 days.

(21) Appl. No.: 12/338,835

(22) Filed: Dec. 18, 2008

(65) Prior Publication Data
US 2009/0228319 A1    Sep. 10, 2009

Related U.S. Application Data

(60) Provisional application No. 61/015,521, filed on Dec. 20, 2007.

(51) Int. Cl.
*C12Q 1/68* (2006.01)
(52) U.S. Cl. ......................................................... 435/6.1
(58) Field of Classification Search .................. None
See application file for complete search history.

(56) References Cited

U.S. PATENT DOCUMENTS

| 7,972,783 | B2 * | 7/2011 | DeNise et al. ............... 435/6.11 |
| 2007/0134701 | A1 | 6/2007 | Denise et al. |

FOREIGN PATENT DOCUMENTS

| WO | WO 2005/052133 A | 6/2005 |
| WO | WO 2005/101230 A | 10/2005 |
| WO | WO 2009/045289 A | 4/2009 |

OTHER PUBLICATIONS

Georges et al., Nature Genetics 4: 206-210 (1993).
Brenneman et al., J. Heredity 87:156-161 (1996).
Drogemuller et al., Mammalian Genome 16: 613-620 (2005).
Database DBSNP [Online] NCBI; Oct. 24, 2007, "Bos Taurus Resequencing" XP002527654 retrieved from NCBI Database accession No. rs41639647, the whole document.

* cited by examiner

*Primary Examiner* — Juliet Switzer
(74) *Attorney, Agent, or Firm* — Judy Jarecki-Black; Chad Kitchen; Merial Limited

(57) ABSTRACT

The presence of horns within commercial cattle populations increases the chances of injuries. The Polled (hornless) condition in cattle has existed since domestication, and it has been selected by breeders because of its economic importance and ease of management. A dominant mutation is believed to cause the polled phenotype. The present invention relates to the identification of breed-specific single nucleotide polymorphisms (SNPs) and their haplotypes, in the bovine genome, in or near gene(s) encoding polypeptides associated with the Polled phenotyped in beef production. The invention further encompasses methods and systems, including network-based processes, to manage the SNP data, haplotype data and other data relating to specific animals and herds of animals, veterinarian care, diagnostic and quality control data and management of livestock which, based on genotyping, have predictable productions quality traits, husbandry conditions, animal welfare, food safety information, audit of existing processes and data from field location.

9 Claims, 21 Drawing Sheets

FIG. 1

A1356048G
[SEQ ID NO. 1]
ACCCACGGACATGTAGAGGCCTTGATATCTCCNNNNNNNNNNNNNNNNNNNNNNNNNNNN
NNNNNNNNNNNNNNNNNNNNTAGAAGCTGTCCTGGGAAAGGGATCTGCCTGGCCAGGAGTGG
TTTGGTGTACAACCTCGGTGCTCACTGAGCGGACTTTGGTTTTCTTGGAAAACTAAAAGACAAGC
CTCTGACTGCTAACCATGTTATCTGTATAACTGGAGATGATTTCAGTGGTATTTCCCTCTT[A/G]A
AAAAAGATAAATTGTGCCACTTGAGTGCAGCTGTCACTGATTGGGTCTATGTGAACAGGATAAAA
GAGTTATGTTCCCCAGCAGCTCTGTGATAAATTGTTGAAGAGCCACAGCAATAAACAAGAAAAGC
TGACCACAGGAATGTCCCAGACAGAAAGGAAAAGGCCAGCAAGGAGGCTCCCTAGGGGGCTGT
CATGGTCTCTCGGGGACCATAGTCAGACTCTCTGCTGTGGTGCAGCCCACACACCA

FIG. 2

A1872077G
[SEQ ID NO. 2]
GGGCTAGCCTGGGAATGTAATAACCCCTTTATAACACTACTCGCATGGGTAAATACATCCAGATT
ACTTATAGATAATTAACAGAAGAATTTTTAGGGCTCAGTCCATTTGGAAGTTTAAGACTGGAAAGT
GAAGACACTCTGTATGATGGGGTTAACATAAAATGCTTTTATGTGTGTTCATACAAAGAACCAAG
GCAATATTTTTCATTAATTTTCCCTGGAGAATAGCTGCTTTACAAAGTTGTGTC[A/G]GCTTCTGC
TCTCAGCAAAGTGAATCACCAAACGGATACATGTATCCTCCCTTTTTTGGATTTCCTCCCGTTTAA
GTCACCAGCAAGCACAGAGGAGAGTTCGCAGTGCTGGACAGTGGGTTTTCATCAGTTATCTATT
CTATAGATAGTATCCATTTTTAAAAATTAAACTGACTCATCATTGGACAAAGAAAATCTTCCTTCAC
AGAAACCCAACTCCACACTAAAATGGGATATAAAGAATTTGTGGC

FIG. 3

T1872200C
[SEQ ID NO. 3]
CTGGAAAGTGAAGACACTCTGTATGATGGGGTTAACATAAAATGCTTTTATGTGTGTTCATACAA
AGAACCAAGGCAATATTTTTCATTAATTTTCCCTGGAGAATAGCTGCTTTACAAAGTTGTGTCAGC
TTCTGCTCTCAGCAAAGTGAATCACCAAACGGATACATGTATCCTCCCTTTTTTGGATTTCCTCCC
GTTTAAGTCACCAGCAAGCACAGAGGAGAGTTCGCAGTGCTGGACAGTGGGTT[T/C]TCATCAG
TTATCTATTCTATAGATAGTATCCATTTTTAAAAATTAAACTGACTCATCATTGGACAAAGAAAATC
TTCCTTCACAGAAACCCAACTCCACACTAAAATGGGATATAAAGAATTTGTGGCAATTATGGTACA
AACACCTAAACCCAGAAGGCAGAAAGTTGGAACGTATTGAATGCATGATACCGTAATGATAAGAA
ATAGTTCTACCATGAAATAACACGTATTTTTCTCTTAGCCTTAAC

FIG. 4

T2101528C
[SEQ ID NO. 4]
CACTAATGTGGAAGTTCATACAGAAAAGAAGGAAGTCAGGAATTAATTTCTAAGCGGATCTGTCT
TACTCCTTTGGATATGAGCGAAGAAACCGATTTGAGCTGGTTTAAGCCCGAAGTGAGTTGGTTGG
GGAGGTAGCCTACGGGTAGAAAGCCATCTTCAGAAGCCAGACCAGGAAAGAAAGCCTCAGGGC
GGGACTAAACTGGAACTTCGCGAGCATGGAGTCTCTCTGTCTGTCTGTCTCTCTGCT[T/C]CTCT
CTCTCCCCTCTACGGCTTTTCTCTGAGCCTGGGCTAGATGGCATACAGTCATCCCCACAACCCAG
GCGATTCTTAAGTTACACTTTTCTGTCCTAACAATTTATAAAGACTACCAATCTGGCAACTTCCTTC
CAAATTCCTACCAGAGAGCTGTTTCTTTGGCTGGACTGGGGTCAGGTAGCCCCCTCCTGTGATCT
GCCTTGGCCAGAGACCATGTGACATGATATGATTATAAACTTGGCTGCC

FIG. 5

T2214142A
[SEQ ID NO. 5]
TGTTTTCCACCGTGTCAGGAATCTGAACTTTGGGGTTCTCTGGGACATAAAAGATGGATGCCAGC
GGGTGAGAACTAACTTCCGTTTCAGTTCAAAATCCATTGCTGGCAGCACCCGTGAGAGGGTCTCT
GCTGTGCTCACATGGGATAGAAAGACCTAGAATGGCAGTTCGGGACCAGCACTCCAGAGCCCTG
ATTCCCAGGACTTCAGTGGACAGAGAACCCCAAACATCGGGAGCCTTTCCAACTCA[T/A]GGGG
GAAGGATGAAACCTAATTTCATTTTACCAGGCAAGTTTTAGCATTTTGCCAGAATTCTTTTCGAGT
TTAAGGCGTGTGAAGACCAGGATAAGTGAACTGTGCTTGAATCAGGTGGCACGTAGGTTTGAAC
GGTGAGGCATCCAGATGGCTTAGAAGCAGTGGTCGCTTGAAGCAGTTACTGAGGACAGGGATA
GTATCCGAGTCACCTCTGTGTCCTCCCAGCCTGAGGTTATGACACCTTGAGTG

FIG. 6

T2220054C
[SEQ ID NO. 6]
TCACAACAGTTATTTGTCCCCAGATGTCAGTAGTCCTGAGATTGAAAAAGTTCCTGGATTCAAAG
CAGAGCAAGTCATGAGATTACAGGTTTTTTCACCTACCAAGTTGGCCTTGACTTTTCAGACCTGAT
ACTCAGCACCAGCAAAGAATCAGGTACTTCCCTGGAGGAAGTGTTATGGCCCCTCTGGAAGACA
GCAGGTCTGGCAGTGTGTATGTCAGAGGTCTTGAAAATGTGTATCAACCTGGAGG[T/C]GGGGG
TTTGGGGAGTCGCCTCAGGATCACCCAGGGAATGGATTTGAAAAAACTCATAAGCCCTCAGAGA
TCCGGGCTGGGGGCTAGGTTGGGAGGAGCTGAGAACTTGTGCACCATTCCAAGAACATAGGTA
GGCACGCAGTGCAGGCTGCTGCTCGTGGGAACAGCCTGATCGTACCACTTGGGGAATGGGTAC
ATGACTTACGGTCACTCCTAGGACAGAGTGATGATCAGCCCTCCAAAATGATGTT

FIG. 7

T2220178A
[SEQ ID NO. 7]
GACCTGATACTCAGCACCAGCAAAGAATCAGGTACTTCCCTGGAGGAAGTGTTATGGCCCCTCT
GGAAGACAGCAGGTCTGGCAGTGTGTATGTCAGAGGTCTTGAAAATGTGTATCAACCTGGAGGC
GGGGGTTTGGGGAGTCGCCTCAGGATCACCCAGGGAATGGATTTGAAAAAACTCATAAGCCCTC
AGAGATCCGGGCTGGGGGCTAGGTTGGGAGGAGCTGAGAACTTGTGCACCATTCCAAG[T/A]A
CATAGGTAGGCACGCAGTGCAGGCTGCTGCTCGTGGGAACAGCCTGATCGTACCACTTGGGGA
ATGGGTACATGACTTACGGTCACTCCTAGGACAGAGTGATGATCAGCCCTCCAAAATGATGTTCT
AAAGGATTTTTACCGATGTGGAGACAGTTCATGCTACATAAATAAAGCAGGTACAAAGCTATATA
TAATTTCAAAGAAGTTAAAAAAACCCAAACCCCAATAAAAACCCAATACACTTAAC

FIG. 8

C2225310T
[SEQ ID NO. 8]
CCAAGCTCCACAACAAGACCCCGCAATGAGAAGCCCACGCACCACAACTAGAGAAAGCCGTCAC
CCAGCAACAAAGACCCAGCACAGCCAAAAATGAAATAAAAACGAAAACAAAAACCGACTAGCCT
CTGTTCTCACCAATTCTTGCCTATCAGATAATGAACAAGCAAACAAATATGCAAAGTGGTGATAA
GTCGCCATCAGAAGCAAGAGCCAGGCAAAAGGACGGTGAGAGTGGAAGGTCTATCTT[C/T]AG
GAAGAGTTGCCAGGGAAGGCCTCTCTGACGTGGCGACATCTGCACGGAGACCAGCAGCACACA
AAGGAGCTTGACGACCACTGGGAAGCCAGACATTTCAATTTTCTCAACGCTTTCCATTAACACCC
CACAAACAAAACCCCTTCCTCTCTCCTAAGCACAAATATTTGCCTTTGGCCCATAGCTGAAAAATT
TTACATAAACCACCGCTTATTTAAACAGACCCACGACCACACGTTGATTCAATA

FIG. 9

G2288436A
[SEQ ID NO. 9]
CCTCTGGACACGCCAGTGCCTCCTGAGCCCAGCTATTGTCCTGCCAGGCCACACATTTCCAAGG
GCAGTGGCTAGCCCTCAGTCACCCTCTCTGGGTTAGTTGCCCATCCCTGGTCCCATCAGCTATGG
CAGGGAGACCGGTGGTATAGAGCCCCTTGGAAGCATCATTCTTAGGACAGCGGTGGCTGTCTTG
GGTGGATTAAGCCAGAGGAAAATTGAGTGTGGGAGGCCAACTGCATGAACACAGGAG[G/A]GT
GAACGTCTAATGAGCTCAGCTCTAATTACTGCTTGNNNNNNNNNNNNNNNNNNNNNNNNNNNN
NNNNNNNNNNNNNNNNNNNNNNNNNNNNNNNNNNNNNNNNNNNNNNNNNNNTGAGCAGTGAGACC
ATTACCACGATCGTTGAAAGAAACCCCCTACCCCTGGGCAGTCACCTTCCTTTGCTTCTCCCCAG
CCCTGGGCAACCACTAAATCTTCTGTCTATGAGTTTGTCTCTTGTGCCACATTTCACAT

FIG. 10

C2332892T
[SEQ ID NO. 10]
ATAGCAAGGAAGAAATGGGCAGGGAAGAGAAAAGAAGCTTTGGGAAGGAAGACAGCTGCTGCT
GCTGCTAAGTTGCTTCAGTCATGTCCGACTCTGTGTGACCCCACAGACAGCAGCCCACCAGGCT
ACCCTGTCCCTGGGATTCTCCAGGCAAGAAAACTGGAGTGGGTGCAAGGAAGACAGGGGACCT
GACAATTGATTGGAGGCGAAGCAAAGAATGGTGAAGAGGTCACGGGCCTCTGGCGTTTCG[C/T
]GGCCAAGACACAAGAAGGACAATGTCACTGAGAACTCAGGAGGCACAGGCAGGGGACAGGGG
TATGCAGGGGGGCCTTGAGAGGAAACCATCCGCATTCATTAGAGACACTCGGCATGCACCTATA
CATAAACGGGAGCCATAGGGCTGCAGGTGGTCGGGAATTCAGAACTGGGTGGGTCTGGGGAGA
CGGCTTAGGGCTGCGGGAGTCAGAGACCCAGCACTGGTCACTGAAGTCACGGCAGGCCGGG

FIG. 11

G2333140A
[SEQ ID NO. 11]
GTTGACAAAAGCTCAGAGTCCTGGGTAGGAAATGTGGGAACTAGAGCTGAGAAGTCATCTGGGG
CCAGATCAGGGGGCGTGGAGTCTCAGATTAAGAGAGCTGTGTTCCGCTTGTGTTTGGGGGAAAT
GCTGAACAGAAGATTCATTTGACAATGGTGTGTTCATTAGATCGAGGGGTAAGAATTAAAGTAGG
AAGACCAACTAAGCAATAACTCGGGCAAGAAACAAGGAAGCCTGAACAAGGATAAAT[G/A]GCA
AGGAAGAAATGGGCAGGGAAGAGAAAAGAAGCTTTGGGAAGGAAGACAGCTGCTGCTGCTGCT
AAGTTGCTTCAGTCATGTCCGACTCTGTGTGACCCCACAGACAGCAGCCCACCAGGCTACCCTGT
CCCTGGGATTCTCCAGGCAAGAAAACTGGAGTGGGTGCAAGGAAGACAGGGGACCTGACAATT
GATTGGAGGCGAAGCAAAGAATGGTGAAGAGGTCACGGGCCTCTGGCGTTTCGCGG

FIG. 12

C2338338T
[SEQ ID NO. 12]
AGGAATTAAGCCCATTCAGCACAACTACTGAGCCTGTGCTCCAGAGCCTGGGAGCCGCAAGCAC
TGAAGCCTGCACACCCTAGACCCCCTGGCTACATAAGTAGCCACTGCAATGGGAAGCCTGCCCA
CCACAGCTAGAGAATAGCTCCAGCTGCTCGTCACAACTAGGGAAAAGGCCATGCAGCAACAAAG
ACCCAGTGTAGCCAAAAAATAAAATAAATAACCATTAAAAAAAAAAAGAGTATTCCAT[C/T]AGG
AAACCTCATCTGAATAAAGAACAAACATATGTTTACACCTGAGCTAAAATATTTAACACTATAAAA
GGACTGCAGCCTTTTCAGTTTATCTTATTAGCTCACAATATATGGCAAACTCAGTTTATTTCTTTGA
GGATAGCAATAATCATTTTTCATAAGCTTATTGATGTCCATTTTGAGTGAATTTCTTTACAGAAAAT
AGGATTAATCATAACCACAAACTGTTTCCACGTTTATTGTGTTGGGA

FIG. 13

T2816109G
[SEQ ID NO. 13]
CCTAAATACCTCCCAAAGGATCTGCTTTCTAATGCCATCATATGAGGATTAGGTTTTAACATATGA
ATTCTTGGGTGGCACATTTAACTCATTGCAACCCCCTCTTCAACAGAGATAAGAAAAGCAACCCT
TTGTCTATACCAGTAAGTTATCCTCATATTAAATATTCCACTCATCTATTTCACTGTCCTGAAAGCC
GCAGATAGCACGGGCAACCCACATCTTCATAAATGCTCATGCTTGCCTACAA[T/G]AGAAGACAT
CAGTAAATCTGAGGTGAAGATGCTTGCCTTCCATGTATTAAAACTCCAGGAACAGGACAGTTAAT
ACTGCAGACTAAAATGGGTGTGTTGGGACTTCTCTGGCCATCCAGAGATGACTGAGCACCTCCA
CTGCAGGGCGCACGGGTTCGATCCCTGGTCGGAGAACTAAGATCCTGCAGGCTTTGCTTTGCAG
CCAAATAAATAAATAAATGAAATGGGTGTGTTGCACTGGCAACTTAAA

FIG. 14

C2816370G
[SEQ ID NO. 14]
AGTAAATCTGAGGTGAAGATGCTTGCCTTCCATGTATTAAAACTCCAGGAACAGGACAGTTAATA
CTGCAGACTAAAATGGGTGTGTTGGGACTTCTCTGGCCATCCAGAGATGACTGAGCACCTCCAC
TGCAGGGCGCACGGGTTCGATCCCTGGTCGGAGAACTAAGATCCTGCAGGCTTTGCTTTGCAGC
CAAATAAATAAATAAATGAAATGGGTGTGTTGCACTGGCAACTTAAATCCCATGAGA[C/G]TGTT
GCCATCAGTGATGGGATTCTCAGAAATGGTGACAGTTGTTGGTAATGCTCTCACAAGAGAATGTG
ATGTTTTTTCAATTTACATGGTTACCCAAATAGGATTCATTGCATATTCAGTTCAGTTCAGTCGCTC
AGTCGTGTCTGATTCTTTGCGACCCCATGAACTGCAGCATGCCAGGCCTCCCCGTCCATCACCAA
CTCCCAAGATCCACCCAAACTCATGTCCCTTGAGTCAGTGATGCCATCC

FIG. 15

HP-1013610
[SEQ ID NO. 15]
CTCCTCCATCCATGGGATTTTCCAGGCAAGAACACTGGAGTGGGTTGCCATTTCCTTCTCCAGGA
GATCTTCCCGACCCAGGGATAAAACCCGGGTCTCCCGCATTGTAGGCAGACACTTTACTGTCTGA
GCCACCAGGGGAGTCCAAGTTTGAAAGTCTGACTCTAAAGCCCATCTACTCTAACAGTGCATGTT
CAGTCTATGTACAACTTGCTTATATTTTTGAGATTATCTTCCATCATAAGAATTG[G/C]TACTACC
TATACTTTCATTAAGAAATAAAAAATGTAGTGCTTAAAAAATGGCAGGGCAGGGACACAGACGCA
GACACAGAGAACAGACTTGTGGACAGAGGGGGAAGGAAAGGGTGGGGCCAATGTACAGAGCA
GCGCTGACACGCACGCCATTGTTATGTACGGCAGGCGACTGAAGGGAAGTTGCTGTGCAACAG
GGAGCTCAGCCCAGCACTCTGCGACAACCTGGACGAGGGGCTGGGAGGTTCAA

FIG. 16

HP-1352705
[SEQ ID NO. 16]
TCTCAGTAATCATTAAGACTGACAAGAAGAGGCCTTTCTACCTCTCCGTCTGCTTAGGACCTCAG
GGACAACTGAAGCCTCCAGGGCGGCGAGTACGGTCAAAATGACAGGGCCTTTTAGGGTAGCCT
GCCTGGGGCAATTTCAGGCTTTCAAGAGAACAACCATAGTGATGAGTCTCATTAGCTGCCCGGG
GGTCAAGAAGAGAAAGACCCCAAGATTTCACACTTGAGAACTTTCTGATACAAACTGT[T/A]AT
GTGTGAGTAGGTGTGGCAGTTTTACTGCTTGTACTGTGAAAACCAATTTGATATTTGAATTTCCCC
ACCTGTGGACGTGGGCTGCTCAACTGGGTGCCTCTAAGTCACTTTCAGACACACTTTCTTCTACT
TGCTGGATCATTTTCTCCCAGGACTGTTGTGGAAACAAGAAACATAGCAACAGGTGAGCATCACC
CCCGGGAGGGCTCTTCTTCTAGCCCTTTTTTCCAGCTAATGAAGCGAAGCACC

FIG. 17

HP-1352905
[SEQ ID NO. 17]
AGAGAAAGACCCCAAGATTTCACACTTGAGAACTTTCTGATACAAACTGTTATGTGTGAGTAGGT
GTGGCAGTTTTACTGCTTGTACTGTGAAAACCAATTTGATATTTGAATTTCCCCACCTGTGGACGT
GGGCTGCTCAACTGGGTGCCTCTAAGTCACTTTCAGACACACTTTCTTCTACTTGCTGGATCATTT
TCTCCCAGGACTGTTGTGGAAACAAGAAACATAGCAACAGGTGAGCATCACCC[C/G]CGGGAG
GGCTCTTCTTCTAGCCCTTTTTCCAGCTAATGAAGCGAAGCACCTGCTGTTTGCCCATCGCAGAG
CCAGGCACTTTGCAGATAGTTGGGTTTTCAAGTACACTCCCAGCACTGCCCAGTTAGCCTGCTCC
CTCACTGAGTGAGTTCACTGTATCACTGTCCCGGAGAATCATTTCACGTCTCCTTATTTCTCCCCC
AAACTCCTCTGCTCCCTCCTTTAGCTGATGACATTTATTAGGAATGGA

FIG. 18

HP-1356048
[SEQ ID NO. 18]
ACCCACGGACATGTAGAGGCCTTGATATCTCCNNNNNNNNNNNNNNNNNNNNNNNNNNNNNNN
NNNNNNNNNNNNNNNNNNNNTAGAAGCTGTCCTGGGAAAGGGATCTGCCTGGCCAGGAGTGG
TTTGGTGTACAACCTCGGTGCTCACTGAGCGGACTTTGGTTTTCTTGGAAAACTAAAAGACAAGC
CTCTGACTGCTAACCATGTTATCTGTATAACTGGAGATGATTTCAGTGGTATTTCCCTCTT[G/A]
AAAAAAGATAAATTGTGCCACTTGAGTGCAGCTGTCACTGATTGGGTCTATGTGAACAGGATAAA
AGAGTTATGTTCCCCAGCAGCTCTGTGATAAATTGTTGAAGAGCCACAGCAATAAACAAGAAAAG
CTGACCACAGGAATGTCCCAGACAGAAAGGAAAAGGCCAGCAAGGAGGCTCCCTAGGGGGCTG
TCATGGTCTCTCGGGGACCATAGTCAGACTCTCTGCTGTGGTGCAGCCCACACACCA

FIG. 19

HP-1431709
[SEQ ID NO. 19]
CAAGGTGTTTTTAGGGAAAGGACAGGGAAATTAGACCTCAGCTTCAGTTCTGCCACAGAACTGT
GTGGCGTTGAGGAGGTTACTAAACCACTCTGAGCTACAGTTTCCTCATCTGGAGAACGGGAATA
ATGCCTACTTTTCAGACTCTTTTGATCATCAGATGAATTAATATATATGAAAGCAGTTTCTGAAGT
GTAGATTCATATCATTAATGAAGTAGGATAATCTTATTTTCTGATTTTTGCAAGGT[G/A]ATCTTG
AGTAACATCACCTTACAAAAATGACATCCTGGAGACCTTTATTCCTCATTGGGTCTTTTTCTCCTC
ATTTGTCAAAGGAAGTTGCTAGACTAGATTTCATGGTTAAAGATGTGTGTGTTTATACATGTGCAT
GTAATTTTGAATAAATCATTTGCCTGAGTAACTTATAAATAACTTTTTCTTGCCAAGCCTATGATAT
TTCTATCTGTGTTTTTAAGATTTGAAGACCAATTCTCAAAGACTC

FIG. 20

HP-1438531
[SEQ ID NO. 20]
CTCAGAGCGACAGTCATAAATTGAGCCTGGAGAGAGTATTGTTTGCTTTTCTAACATGTTTTTCTT
CTTTCCAGTGCACATCAGCCTCGTGTTTGGTATTTCGTATGTTGCGCCTGGTAAGAGATTTTCTTG
ACTTAACAAAATTTTGTCTAAGGGTGTGAGTGGGGGAGCAACCATTTAGAAGTCAAAAAATGTGG
GAAATTGGATTTCTGAGTCCAAATCTGTTGCCATTTTGTTTGAATCTTTTTCC[T/C]CAAATACTT
TCTCTGTAGAAGGAGAATTTAGCCAATTCTGATTTTCACATTTGTCTCATAAAACTATTACAGGAA
ATTAACACTAGAGTTAATTTTTAAACCCCTTAAAGGAATTGTTCTTGTGGTTGTCGTTTAGTCGCT
CAGTCGTTCGATTCTTTTGTGACCCCATGGACTGTAGCCCACCAGACTCTTCTGTGTATGGGATT
CTCCAGGCAAGAATACTGGAGTGGGTTGCCACTTCTCCCCCAGG

FIG. 21

HP-1731905
[SEQ ID NO. 21]
TGGTTGAAGTGGGAAGAGGGTGAGTGAGGACCCTAGAGGCAGGAGAAGGTTACAAGAAAGGCA
CCCCACCTCTCCCAGCAACTTGGCATTGCCCTTCTCTCGATCCGCCAGGGCTGAGCCTTGCAGTA
CCCTTAGGGACCACCCGAATTCCTCAGAACACAGTTTGGAAACCACTTAGTGGCTCTTTTCCTTC
TCCTTCATCCATGCATCTTCCAAAGACTTTCCAAGCTCCTCACTTGGAGGGGTATTC[A/G]AGGT
GCTATGAGACATGAAAATGCCCACATCATCCTTTCCGTCCTCAGTAGAGCAGAGGCTGTCTATCT
AGAAAAGGCTGGATCAGAGCTTTGTTGGAGAATTGCTGAACAATGCAACGAAATGAGTATGTCT
GGGGGTGGGCAACAGCAGGAAGTAGTTGTTCTGTGTGGGTTTGAGGAACAGCAACTCTCTCAGA
GATGGAGACGCTTAACCAGAGAGGAGTAACTCTGGGCCCTGGAAGAAACCTAC

FIG. 22

HP-1872077
[SEQ ID NO. 22]
GGGCTAGCCTGGGAATGTAATAACCCCTTTATAACACTACTCGCATGGGTAAATACATCCAGATT
ACTTATAGATAATTAACAGAAGAATTTTTAGGGCTCAGTCCATTTGGAAGTTTAAGACTGGAAAGT
GAAGACACTCTGTATGATGGGGTTAACATAAAATGCTTTTATGTGTGTTCATACAAAGAACCAAG
GCAATATTTTTCATTAATTTTCCCTGGAGAATAGCTGCTTTACAAAGTTGTGTC[A/G]GCTTCTG
CTCTCAGCAAAGTGAATCACCAAACGGATACATGTATCCTCCCTTTTTTGGATTTCCTCCCGTTTA
AGTCACCAGCAAGCACAGAGGAGAGTTCGCAGTGCTGGACAGTGGGTTTTCATCAGTTATCTATT
CTATAGATAGTATCCATTTTTAAAAATTAAACTGACTCATCATTGGACAAAGAAAATCTTCCTTCAC
AGAAACCCAACTCCACACTAAAATGGGATATAAAGAATTTGTGGC

FIG. 23

HP-1872200
[SEQ ID NO. 23]
CTGGAAAGTGAAGACACTCTGTATGATGGGGTTAACATAAAATGCTTTTATGTGTGTTCATACAA
AGAACCAAGGCAATATTTTTCATTAATTTTCCCTGGAGAATAGCTGCTTTACAAAGTTGTGTCAGC
TTCTGCTCTCAGCAAAGTGAATCACCAAACGGATACATGTATCCTCCCTTTTTTGGATTTCCTCCC
GTTTAAGTCACCAGCAAGCACAGAGGAGAGTTCGCAGTGCTGGACAGTGGGTT[T/C]TCATCA
GTTATCTATTCTATAGATAGTATCCATTTTTAAAAATTAAACTGACTCATCATTGGACAAAGAAAAT
CTTCCTTCACAGAAACCCAACTCCACACTAAAATGGGATATAAAGAATTTGTGGCAATTATGGTAC
AAACACCTAAACCCAGAAGGCAGAAAGTTGGAACGTATTGAATGCATGATACCGTAATGATAAGA
AATAGTTCTACCATGAAATAACACGTATTTTTCTCTTAGCCTTAAC

FIG. 24

HP-2101528
[SEQ ID NO. 24]
CACTAATGTGGAAGTTCATACAGAAAAGAAGGAAGTCAGGAATTAATTTCTAAGCGGATCTGTCT
TACTCCTTTGGATATGAGCGAAGAAACCGATTTGAGCTGGTTTAAGCCCGAAGTGAGTTGGTTGG
GGAGGTAGCCTACGGGTAGAAAGCCATCTTCAGAAGCCAGACCAGGAAAGAAAGCCTCAGGGC
GGGACTAAACTGGAACTTCGCGAGCATGGAGTCTCTCTGTCTGTCTGTCTCTCTGCT[C/T]CTC
TCTCTCCCCTCTACGGCTTTTCTCTGAGCCTGGGCTAGATGGCATACAGTCATCCCCACAACCCA
GGCGATTCTTAAGTTACACTTTTCTGTCCTAACAATTTATAAAGACTACCAATCTGGCAACTTCCT
TCCAAATTCCTACCAGAGAGCTGTTTCTTTGGCTGGACTGGGGTCAGGTAGCCCCCTCCTGTGAT
CTGCCTTGGCCAGAGACCATGTGACATGATATGATTATAAACTTGGCTGCC

FIG. 25

HP-2128551
[SEQ ID NO. 25]
CCCACTCTCATCCTCAGTGGGCCATCCTAAAGCAGCATCTTTCCTGAGAGAAAGAAGAGGGCTT
GGTGGGAGCAGCCTTTTCTGTCCTTTTTTTTTTCCGGCCATTGTATGCAGCGTGTGAGATCTCAG
TTCCCCGACCAGCGATTGAACCCGCGCCTCCTGCACTGGGAGCTTGGAGTGTTAACCACTGGAC
CTCCAGGGAAGTCTCCAGCCTCTTCCATGCTGAGTCTTGCACCTTTCTCCACTGACT[T/C]CCCC
CCTTTCTAACGCACACCAGTTTTGTGGTTAACCGGTTGCAGTCCCAAAGTAATTGCTGTTCCATGA
GGAGGTCACACCTCCAGGCATGGAGGGCCTGAGAGAAGTGTAGGTAATTACAGGTTCCTGGGA
ATACTTGAAAAACTTGTTGGAAAGACAGCAGTGTGCTAGCAAAGACATTTAGCCAACGGTCAGG
GATGAAATTTTGGAAAATTCTGCACTGCCACCACAATGCAGTAATTCATTCAA

FIG. 26

HP-2214142
[SEQ ID NO. 26]
TGTTTTTCCACCGTGTCAGGAATCTGAACTTTGGGGTTCTCTGGGACATAAAAGATGGATGCCAGC
GGGTGAGAACTAACTTCCGTTTCAGTTCAAAATCCATTGCTGGCAGCACCCGTGAGAGGGTCTCT
GCTGTGCTCACATGGGATAGAAAGACCTAGAATGGCAGTTCGGGACCAGCACTCCAGAGCCCTG
ATTCCCAGGACTTCAGTGGACAGAGAACCCCAAACATCGGGAGCCTTTCCAACTCA[A/T]GGG
GGAAGGATGAAACCTAATTTCATTTTACCAGGCAAGTTTTAGCATTTTGCCAGAATTCTTTTCGAG
TTTAAGGCGTGTGAAGACCAGGATAAGTGAACTGTGCTTGAATCAGGTGGCACGTAGGTTTGAA
CGGTGAGGCATCCAGATGGCTTAGAAGCAGTGGTCGCTTGAAGCAGTTACTGAGGACAGGGAT
AGTATCCGAGTCACCTCTGTGTCCTCCCAGCCTGAGGTTATGACACCTTGAGTG

FIG. 27

HP-2220054
[SEQ ID NO. 27]
TCACAACAGTTATTTGTCCCCAGATGTCAGTAGTCCTGAGATTGAAAAAGTTCCTGGATTCAAAG
CAGAGCAAGTCATGAGATTACAGGTTTTTTCACCTACCAAGTTGGCCTTGACTTTTCAGACCTGAT
ACTCAGCACCAGCAAAGAATCAGGTACTTCCCTGGAGGAAGTGTTATGGCCCCTCTGGAAGACA
GCAGGTCTGGCAGTGTGTATGTCAGAGGTCTTGAAAATGTGTATCAACCTGGAGG[C/T]GGGG
GTTTGGGGAGTCGCCTCAGGATCACCCAGGGAATGGATTTGAAAAAACTCATAAGCCCTCAGAG
ATCCGGGCTGGGGGCTAGGTTGGGAGGAGCTGAGAACTTGTGCACCATTCCAAGAACATAGGT
AGGCACGCAGTGCAGGCTGCTGCTCGTGGGAACAGCCTGATCGTACCACTTGGGGAATGGGTA
CATGACTTACGGTCACTCCTAGGACAGAGTGATGATCAGCCCTCCAAAATGATGTT

FIG. 28

HP-2220178
[SEQ ID NO. 28]
GACCTGATACTCAGCACCAGCAAAGAATCAGGTACTTCCCTGGAGGAAGTGTTATGGCCCCTCT
GGAAGACAGCAGGTCTGGCAGTGTGTATGTCAGAGGTCTTGAAAATGTGTATCAACCTGGAGGC
GGGGGTTTGGGGAGTCGCCTCAGGATCACCCAGGGAATGGATTTGAAAAAACTCATAAGCCCTC
AGAGATCCGGGCTGGGGGCTAGGTTGGGAGGAGCTGAGAACTTGTGCACCATTCCAAG[A/T]A
CATAGGTAGGCACGCAGTGCAGGCTGCTGCTCGTGGGAACAGCCTGATCGTACCACTTGGGGA
ATGGGTACATGACTTACGGTCACTCCTAGGACAGAGTGATGATCAGCCCTCCAAAATGATGTTCT
AAAGGATTTTTACCGATGTGGAGACAGTTCATGCTACATAAATAAAGCAGGTACAAAGCTATATA
TAATTTCAAAGAAGTTAAAAAAACCCAAACCCCAATAAAAACCCAATACACTTAAC

FIG. 29

HP-2225310
[SEQ ID NO. 29]
CCAAGCTCCACAACAAGACCCCGCAATGAGAAGCCCACGCACCACAACTAGAGAAAGCCGTCAC
CCAGCAACAAAGACCCAGCACAGCCAAAAATGAAATAAAAACGAAAACAAAAACCGACTAGCCT
CTGTTCTCACCAATTCTTGCCTATCAGATAATGAACAAGCAAACAAATATGCAAAGTGGTGATAA
GTCGCCATCAGAAGCAAGAGCCAGGCAAAAGGACGGTGAGAGTGGAAGGTCTATCTT[T/C]AG
GAAGAGTTGCCAGGGAAGGCCTCTCTGACGTGGCGACATCTGCACGGAGACCAGCAGCACACA
AAGGAGCTTGACGACCACTGGGAAGCCAGACATTTCAATTTTCTCAACGCTTTCCATTAACACCC
CACAAACAAAACCCCTTCCTCTCTCCTAAGCACAAATATTTGCCTTTGGCCCATAGCTGAAAAATT
TTACATAAACCACCGCTTATTTAAACAGACCCACGACCACACGTTGATTCAATA

FIG. 30

HP-2288436
[SEQ ID NO. 30]
CCTCTGGACACGCCAGTGCCTCCTGAGCCCAGCTATTGTCCTGCCAGGCCACACATTTCCAAGG
GCAGTGGCTAGCCCTCAGTCACCCTCTCTGGGTTAGTTGCCCATCCCTGGTCCCATCAGCTATGG
CAGGGAGACCGGTGGTATAGAGCCCCTTGGAAGCATCATTCTTAGGACAGCGGTGGCTGTCTTG
GGTGGATTAAGCCAGAGGAAAATTGAGTGTGGGAGGCCAACTGCATGAACACAGGAG[G/A]G
TGAACGTCTAATGAGCTCAGCTCTAATTACTGCTTGNNNNNNNNNNNNNNNNNNNNNNNNNNN
NNNNNNNNNNNNNNNNNNNNNNNNNNNNNNNNNNNNNNNNNNNNNNNNNNTGAGCAGTGAGA
CCATTACCACGATCGTTGAAAGAAACCCCCTACCCCTGGGCAGTCACCTTCCTTTGCTTCTCCCC
AGCCCTGGGCAACCACTAAATCTTCTGTCTATGAGTTTGTCTCTTGTGCCACATTTCACAT

FIG. 31

HP-2332892
[SEQ ID NO. 31]
ATAGCAAGGAAGAAATGGGCAGGGAAGAGAAAAGAAGCTTTGGGAAGGAAGACAGCTGCTGCT
GCTGCTAAGTTGCTTCAGTCATGTCCGACTCTGTGTGACCCCACAGACAGCAGCCCACCAGGCT
ACCCTGTCCCTGGGATTCTCCAGGCAAGAAAACTGGAGTGGGTGCAAGGAAGACAGGGGACCT
GACAATTGATTGGAGGCGAAGCAAAGAATGGTGAAGAGGTCACGGGCCTCTGGCGTTTCG**[C/T
]**GGCCAAGACACAAGAAGGACAATGTCACTGAGAACTCAGGAGGCACAGGCAGGGGACAGGGG
TATGCAGGGGGGCCTTGAGAGGAAACCATCCGCATTCATTAGAGACACTCGGCATGCACCTATA
CATAAACGGGAGCCATAGGGCTGCAGGTGGTCGGGAATTCAGAACTGGGTGGGTCTGGGGAGA
CGGCTTAGGGCTGCGGGAGTCAGAGACCCAGCACTGGTCACTGAAGTCACGGCAGGCCGGG

FIG. 32

HP-2333140
[SEQ ID NO. 32]
GTTGACAAAAGCTCAGAGTCCTGGGTAGGAAATGTGGGAACTAGAGCTGAGAAGTCATCTGGGG
CCAGATCAGGGGGCGTGGAGTCTCAGATTAAGAGAGCTGTGTTCCGCTTGTGTTTGGGGGAAAT
GCTGAACAGAAGATTCATTTGACAATGGTGTGTTCATTAGATCGAGGGGTAAGAATTAAAGTAGG
AAGACCAACTAAGCAATAACTCGGGCAAGAAACAAGGAAGCCTGAACAAGGATAAAT[A/G]GC
AAGGAAGAAATGGGCAGGGAAGAGAAAAGAAGCTTTGGGAAGGAAGACAGCTGCTGCTGCTGC
TAAGTTGCTTCAGTCATGTCCGACTCTGTGTGACCCCACAGACAGCAGCCCACCAGGCTACCCTG
TCCCTGGGATTCTCCAGGCAAGAAAACTGGAGTGGGTGCAAGGAAGACAGGGGACCTGACAATT
GATTGGAGGCGAAGCAAAGAATGGTGAAGAGGTCACGGGCCTCTGGCGTTTCGCGG

FIG. 33

HP-2338338
[SEQ ID NO. 33]
AGGAATTAAGCCCATTCAGCACAACTACTGAGCCTGTGCTCCAGAGCCTGGGAGCCGCAAGCAC
TGAAGCCTGCACACCCTAGACCCCCTGGCTACATAAGTAGCCACTGCAATGGGAAGCCTGCCCA
CCACAGCTAGAGAATAGCTCCAGCTGCTCGTCACAACTAGGGAAAAGGCCATGCAGCAACAAAG
ACCCAGTGTAGCCAAAAAATAAAATAAATAACCATTAAAAAAAAAAAGAGTATTCCAT[T/C]AGG
AAACCTCATCTGAATAAAGAACAAACATATGTTTACACCTGAGCTAAAATATTTAACACTATAAAA
GGACTGCAGCCTTTTCAGTTTATCTTATTAGCTCACAATATATGGCAAACTCAGTTTATTTCTTTGA
GGATAGCAATAATCATTTTTCATAAGCTTATTGATGTCCATTTTGAGTGAATTTCTTTACAGAAAAT
AGGATTAATCATAACCACAAACTGTTTCCACGTTTATTGTGTTGGGA

FIG. 34

HP-2640799
[SEQ ID NO. 34]
TGTGAGTGTCCAAGAGTCTGCAGTGGATGCACGGGAAGACACTGGCCTGCCACGGGTCAGGGG
CACTGAATACAAGAGTTCCAGGAGCCATGGTGTGCTGGCCTACGTCCTTTTGAAGGAGGTTGCC
ATTACCCCTACCGTAGTTTGGCCTCACAGGGAGGGAACACAGCTCCATCCATCAACAGAAAACTG
GACATCTCTGTTGCTTACCCTCAAAGGACCTAAACAGCAACCCAGGCTTTTTCAGAGT[T/A]TGA
TTACCCAGAAGAGCTAAGAACAGACTGGATGTGAGTTTTTGTTCTATTTTCAGAACCAAGCACTC
TGCACCATCACAAATTGCTGATGAGCACAAGTAATTTTAGTTCAGATCTCTACCAGTGAATTTTCT
TTCTTTGGACATCACAAATATTGCATTAGTATCCAAAAAGGACTTTGAAAACATCCTTGGAGCTCT
TTGAAGTCTGTGTGAGGGTCTTGAATATCCCTATGACTCATGAGCAAAAG

FIG. 35

HP-2648129
[SEQ ID NO. 35]
TTGAAGTGAATTGCAAACCAAACAAGAGAACAAACTGCAGTCATTTCCTGGATCTGAAACCAAAT
CTTAATATGAACTGTTTACTGAAATGTGAACCAGCTAAAGTTTGAGAGTAATTTCCAAACACACCT
GAGGATTTGGTCTAATCACGTAACCGAACCCATATATATTTAAAAGCTTTTGAACAGACTTGGAAA
CTCACATTGCTAAACAAATCTCAGAACAAACTCAAATGAAACTAATAGTTCTT[T/C]ACAGTGAG
CTGACTAAGGAACACACAATAGAAATGTGATGATCGACCTTCTTTTTTCCGAGTCAACATTATAAT
GAGTTGAGTTTTAACACAATTCAGTCTGCAATTATTTTTCCAAGAGGGACTATACGATCCTTTTGA
TAGGTGTGTATTGTGTGCAGGAGGAGGAAGGAGGAAGTTAGGGGGTCGGGATTATAATGGACA
AGGAAAGGACTCAGAGGCGATGAAGCGAAGTGTGTCCTTAGAGACGG

FIG. 36

HP-2650867
[SEQ ID NO. 36]
CTTCAAACGTCCCTATTGCTAATTTTCTCCTCTCTCTTTCTACCATATGCTGTCCCTCCCGTTCAGA
ACTTAATGAACAACGTGCCTCAGTCTGCTGGTCCCCATTCTGAGCCCCTTTCACCCACTTCATGC
CAGATGACTGCTCTGCAAATTATTTGGCCACAGAAAGTTTATCCACCCAACATCTAGTCTTGTCTT
GAGGATGGTGTTCCACTAAGCACACACAGGGAAATGCTGCTTTAAACAGTGC[T/A]GGATATGC
TTTGTTCATTCTTACCTGCATTTCCTTTTTAAGAATTTAAATATTTATTTAGTTATTTATTTTGGCTG
TGCTGGGTTGTTGTTGCTGAGCGGGTGGGGCTACTGTCGTTACGGTGCACAGGCTTCTCATTG
CAGAAAGCAGACCCCAGGGCACTCAGGCTTCGGTGGTTGCAGCGAGTGGGTTCCATAGTTGTG
GCACATTGACTTGGTTACCCTGCAGCACGTGGAATCTTCCTGGGTCA

FIG. 37

HP-2651006
[SEQ ID NO. 37]
GTGCATTGAAGGTTCTCAAACAGGTTAGTTCCCCTAATCCCCTTTTCCTCTGCCGCCAGACTACCT
CTCCTCCCGGCTTCCTGGCTTCTGTTACATCACCACCATCGTCCGGCTTTCCACGCTGCGTCTTG
GCGTCTCCCCTTCAAACGTCCCTATTGCTAATTTTCTCCTCTCTCTTTCTACCATATGCTGTCCCTC
CCGTTCAGAACTTAATGAACAACGTGCCTCAGTCTGCTGGTCCCCATTCTGA[G/T]CCCCTTTCA
CCCACTTCATGCCAGATGACTGCTCTGCAAATTATTTGGCCACAGAAAGTTTATCCACCCAACATC
TAGTCTTGTCTTGAGGATGGTGTTCCACTAAGCACACACAGGGAAATGCTGCTTTAAACAGTGCT
GGATATGCTTTGTTCATTCTTACCTGCATTTCCTTTTTAAGAATTTAAATATTTATTTAGTTATTTAT
TTTGGCTGTGCTGGGTTGTTGTTGCTGAGCGGGTGGGGGCTA

FIG. 38

HP-2657651
[SEQ ID NO. 38]
ATGCATGCATGCTAAGGCGCTTCAGCCGTGTCTGACTTTGTGCGACCCTACAGACAGCAGGCCA
CCAGCCTCCTCTGTCCACGGGATTCTCTAGGCAACAAAACTGGAGTGGGTTGCCATTTCCTTCTC
CAAGGTGGCTGTCTACAAGCCAGGAAAAGAAACCTCAGTGGAACTTGACCACGCTGGCATCCTG
ATCCAGACTTCCAGCCTCCAGAACTGTGAGAAAATTAACTTCTGGTGGTTAAACCAC[G/C]CCTT
CGGGTTATGGTAGTCAAGCTAAGACACTTGCTTATAGGTGACCTAGAAGTCTCACCTTTAAACCA
ATAAAGCATGTCAGAAGACACTGTGCAGAGATCAAATGTGGCTGCTCAGGTGGGTTAAATTCAA
GAAGGCATCAGGGACTTCCCTGGCAGTTCAGTGGTTGAGATTTTGCCATTCAATGCACGGGGTC
CAGGTTCAGCCCCTGGTTGGGGAGGTAAGATCCCACAGGGCTCATAGCCAAGA

FIG. 39

HP-2676311
[SEQ ID NO. 39]
CTGCCATATCACTAAACAAAGGATGTCGCAGACATCAGTAATTGCAGCCATCATAAATGGTGAGC
TAGTGAGCCCTGAGGGAACTCAGGAAGGAAAGAATAGCTGCCATCTAGTAGCCATCAGACCACA
GCCACTCCCTGCAGTGAGCCCTGAGGACCCTCAAGATGTGAAAATACAGGATCCCGGCCCCCCC
GAGACTGGAAGTGCTTATCAAAGGAGTGAGTTCAGTGAGGCCAGACTCTTGCTCTTC[T/C]CAT
ACACCGCAAGGTGCTAAATTCCTTAACTTGGGACAGCTGGTTTTCTTTAATTTATAATAATCTTTT
GACGTTCAGACTACCTGCCTTTGTAGGTAGTCACATACTTCTACATAACCTAGCTCTCCTCCTCAC
CTCCCTGGAGCAGTTCCTTCAGGGTTATTTGATATGTTTCCTCCTGGGCTTGAAGTCCTAAAAATT
CCTGCCGATTAAAACATAACTCTCAACTTTTAAGTTGTGAACATTTTTT

FIG. 40

HP-2816109
[SEQ ID NO. 40]
CCTAAATACCTCCCAAAGGATCTGCTTTCTAATGCCATCATATGAGGATTAGGTTTTAACATATGA
ATTCTTGGGTGGCACATTTAACTCATTGCAACCCCCTCTTCAACAGAGATAAGAAAAGCAACCCT
TTGTCTATACCAGTAAGTTATCCTCATATTAAATATTCCACTCATCTATTTCACTGTCCTGAAAGCC
GCAGATAGCACGGGCAACCCACATCTTCATAAATGCTCATGCTTGCCTACAA[T/G]AGAAGACA
TCAGTAAATCTGAGGTGAAGATGCTTGCCTTCCATGTATTAAAACTCCAGGAACAGGACAGTTAA
TACTGCAGACTAAAATGGGTGTGTTGGGACTTCTCTGGCCATCCAGAGATGACTGAGCACCTCC
ACTGCAGGGCGCACGGGTTCGATCCCTGGTCGGAGAACTAAGATCCTGCAGGCTTTGCTTTGCA
GCCAAATAAATAAATAAATGAAATGGGTGTGTTGCACTGGCAACTTAAA

FIG. 41

HP-2816370
[SEQ ID NO. 41]
AGTAAATCTGAGGTGAAGATGCTTGCCTTCCATGTATTAAAACTCCAGGAACAGGACAGTTAATA
CTGCAGACTAAAATGGGTGTGTTGGGACTTCTCTGGCCATCCAGAGATGACTGAGCACCTCCAC
TGCAGGGCGCACGGGTTCGATCCCTGGTCGGAGAACTAAGATCCTGCAGGCTTTGCTTTGCAGC
CAAATAAATAAATAAATGAAATGGGTGTGTTGCACTGGCAACTTAAATCCCATGAGA[C/G]TGTT
GCCATCAGTGATGGGATTCTCAGAAATGGTGACAGTTGTTGGTAATGCTCTCACAAGAGAATGTG
ATGTTTTTTCAATTTACATGGTTACCCAAATAGGATTCATTGCATATTCAGTTCAGTTCAGTCGCTC
AGTCGTGTCTGATTCTTTGCGACCCCATGAACTGCAGCATGCCAGGCCTCCCCGTCCATCACCAA
CTCCCAAGATCCACCCAAACTCATGTCCCTTGAGTCAGTGATGCCATCC

FIG. 42

HP-2820224
[SEQ ID NO. 42]
TTAATACGGGGAAGAATTTTACTAGATGTTTTAAATTTTGGAGTTGCCTGAGTATAAATGCCTCTA
GACAGCTCCCCAAACCATGCTTTATAGACTGCTAAAGCAGTTCTTTTTTTTTTTTTTTTTCTTATTT
CTTGGTCACAGTGAGTTTCTCTCATTGAGTTAAATACATATGGTTTGGAATACAGTTAAGTCCCCT
ACATACAAATGAGTTCCATTTTGAGAGTGCGTTCGTAAAGCCAATTTTTTC[T/G]CAAGTCCAAC
AAAGTTAGCCTAGGTACCTACTCAACTAACACAGTCGTGCATATAGGACTGTACTATGACAGGTT
TATAATACTTTTCACCCAAATAATACATGAAAAACAAGCAAAGTATAAAGAAACCTTAAAAAATAT
ATTTATTTATTCATTTGTCTGCACTGGGTCTTTAGTTGTAGCGTGTGAACTCTTGCTGCCTGTGGG
ATCTAGTTCCCTGACCAGGATTTGAAACCAGGGGACCTGCATT

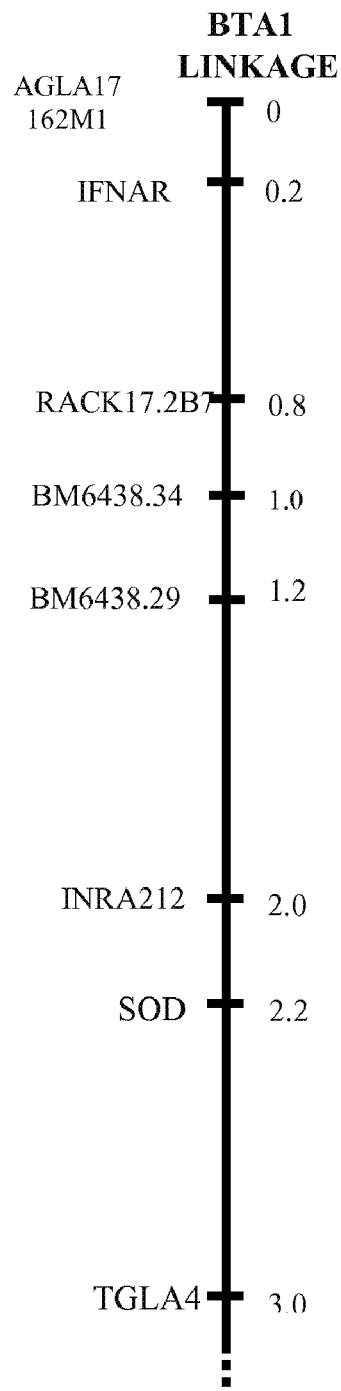
FIG. 43. Linkage Map of Bovine Chromosome 1

FIG. 44. *Polled* SNP Allele Frequencies in Bovine breeds

| SNP | Combined | Angus | Brahman | Charolais | Gelbvieh | Hereford | Holstein | Jersey | Limousin | Red Angus | Simmental |
|---|---|---|---|---|---|---|---|---|---|---|---|
| G49284C | 0.09 | 0.19 | 0.10 | 0.03 | 0.06 | 0.00 | 0.22 | 0.00 | 0.03 | 0.21 | 0.07 |
| T39385A | 0.19 | 0.18 | 0.37 | 0.20 | 0.25 | 0.13 | 0.44 | 0.05 | 0.09 | 0.13 | 0.17 |
| A39381G | 0.36 | 0.46 | 0.03 | 0.34 | 0.25 | 0.65 | 0.28 | 0.10 | 0.20 | 0.39 | 0.39 |
| C39382G | 0.19 | 0.18 | 0.37 | 0.18 | 0.25 | 0.13 | 0.44 | 0.05 | 0.09 | 0.13 | 0.17 |
| G69199A | 0.05 | 0.00 | 0.03 | 0.14 | 0.00 | 0.00 | 0.33 | 0.00 | 0.06 | 0.00 | 0.04 |
| T69211C | 0.09 | 0.00 | | 0.00 | 0.03 | 0.00 | 0.39 | 0.00 | 0.03 | 0.00 | 0.11 |
| A43281G | 0.07 | 0.00 | 0.46 | 0.02 | 0.00 | 0.09 | 0.44 | 0.05 | 0.03 | 0.00 | 0.02 |
| A10273G | 0.11 | 0.01 | 0.03 | 0.18 | 0.09 | 0.03 | 0.28 | 0.10 | 0.34 | 0.00 | 0.20 |
| T10275C | 0.12 | 0.00 | 0.07 | 0.18 | 0.09 | 0.06 | 0.28 | 0.10 | 0.34 | 0.00 | 0.20 |
| T100032C | 0.30 | 0.11 | 0.07 | 0.41 | 0.28 | 0.57 | 0.11 | 0.85 | 0.22 | 0.18 | 0.22 |
| T9868C | 0.33 | 0.79 | 0.10 | 0.06 | 0.33 | 0.00 | 0.22 | 0.00 | 0.34 | | 0.48 |
| T49320A | 0.18 | 0.30 | 0.00 | 0.09 | 0.09 | 0.27 | 0.00 | 0.25 | 0.19 | 0.26 | 0.13 |
| T49278C | 0.19 | 0.29 | 0.23 | 0.09 | 0.09 | 0.27 | 0.00 | 0.25 | 0.19 | 0.26 | 0.13 |
| T49279A | 0.17 | 0.28 | 0.00 | 0.09 | 0.09 | 0.27 | 0.00 | 0.25 | 0.19 | 0.26 | 0.13 |
| C49249T | 0.18 | 0.28 | 0.03 | 0.09 | 0.09 | 0.27 | 0.00 | 0.25 | 0.19 | 0.26 | 0.13 |
| G44231A | 0.44 | 0.26 | | | 0.41 | 0.52 | 0.39 | 0.05 | 0.47 | 0.26 | 0.50 |
| C79182T | 0.17 | 0.01 | 0.30 | 0.24 | 0.13 | 0.11 | 0.44 | 0.05 | 0.44 | 0.00 | 0.22 |
| G69234A | 0.36 | 0.71 | 0.03 | 0.33 | 0.41 | 0.23 | 0.44 | 0.00 | 0.19 | 0.58 | 0.33 |
| C59230T | 0.12 | 0.19 | 0.00 | 0.13 | 0.10 | 0.23 | | 0.00 | 0.00 | 0.13 | 0.07 |
| A15434T | 0.11 | 0.00 | 0.00 | 0.11 | 0.03 | 0.52 | 0.00 | 0.00 | 0.06 | 0.00 | 0.02 |
| T15431A | 0.15 | 0.24 | 0.00 | 0.12 | 0.31 | 0.02 | 0.00 | 0.55 | 0.03 | 0.26 | 0.09 |
| G15428C | 0.20 | 0.24 | 0.73 | 0.12 | 0.31 | 0.02 | 0.00 | 0.55 | 0.00 | 0.26 | 0.09 |
| C15424T | 0.05 | 0.00 | 0.08 | 0.06 | 0.00 | 0.03 | 0.00 | 0.55 | 0.00 | 0.00 | 0.00 |
| T110337G | 0.12 | 0.00 | 0.00 | 0.09 | 0.06 | | 0.22 | 0.00 | 0.09 | 0.03 | 0.07 |
| C110341G | 0.11 | 0.01 | 0.00 | 0.09 | 0.06 | 0.44 | 0.22 | 0.00 | 0.09 | 0.03 | 0.07 |
| T110336G | 0.09 | 0.00 | 0.43 | 0.00 | 0.00 | | 0.13 | 0.00 | 0.00 | 0.00 | 0.00 |
| A34585C | 0.19 | 0.20 | 0.17 | 0.27 | 0.28 | | 0.00 | 0.00 | 0.06 | 0.24 | 0.13 |
| T69220G | 0.04 | 0.00 | 0.00 | 0.06 | 0.03 | 0.02 | 0.33 | 0.00 | 0.03 | 0.00 | 0.04 |

FIG. 45

Mode of *Poll* Inheritance

| Genotype | Males | Females |
|---|---|---|
| PP ScSc | Scurred | Scurred |
| PP Scsc | Polled | Polled |
| PP scsc | Polled | Polled |
| Pp ScSc | Scurred | Scurred |
| Pp Scsc | Scurred | Polled |
| Pp scsc | Polled | Polled |
| pp ScSc | Horned | Horned |
| pp Scsc | Horned | Horned |
| pp scsc | Horned | Horned |

Horned = Hollow, bony growths that are fused to the skull. Sinus cavity pervades into the horn
Scurred = Loose, "cartilaginous" growths
Polled = No growths

FIG. 46

Sequence of *Bos Taurus* Chromosome 1 (bases 1 thru 3,000,000)
[SEQ ID NO. 43]
(See electronic compact disk sequence listing. File name: Btaurus Chm 1 seq.txt)

FIG. 47

Comparison of horn/poll marker coordinates in successive releases of the bovine genome sequence. Markers in the disclosure are identified by their location in Btau3.0

| Btau3.0 coordinate | Btau3.1 coordinate | Btau4.0 coordinate |
|---|---|---|
| 1013610 | NA | 1008610 |
| 1352705 | 306920 | 1338205 |
| 1352905 | 307119 | 1338405 |
| 1356048 | 310281 | 1341564 |
| 1431709 | 385924 | 1417209 |
| 1438531 | 392746 | 1424031 |
| 1731905 | 686119 | 1717404 |
| 1872077 | 826293 | 1857578 |
| 1872200 | 826414 | 1857700 |
| 2101528 | 1055743 | 2087001 |
| 2128551 | 1082763 | 2114048 |
| 2214142 | 1168357 | 2199642 |
| 2220054 | 1174270 | 2205555 |
| 2220178 | 1174392 | 2205678 |
| 2225310 | 1179524 | 2210809 |
| 2288436 | 1242651 | 2273936 |
| 2332892 | 1287109 | 2318392 |
| 2333140 | 1287355 | 2318640 |
| 2338338 | 1292598 | 2323838 |
| 2640799 | 1595014 | 2626299 |
| 2648129 | 1602344 | 2633629 |
| 2650867 | 1605081 | 2636366 |
| 2651006 | 1605221 | 2636506 |
| 2657651 | 1611869 | 2643153 |
| 2676311 | 1630524 | 2661809 |
| 2816109 | 1770324 | 2801609 |
| 2816370 | 1770584 | 2801870 |
| 2820224 | 1774439 | 2805724 |

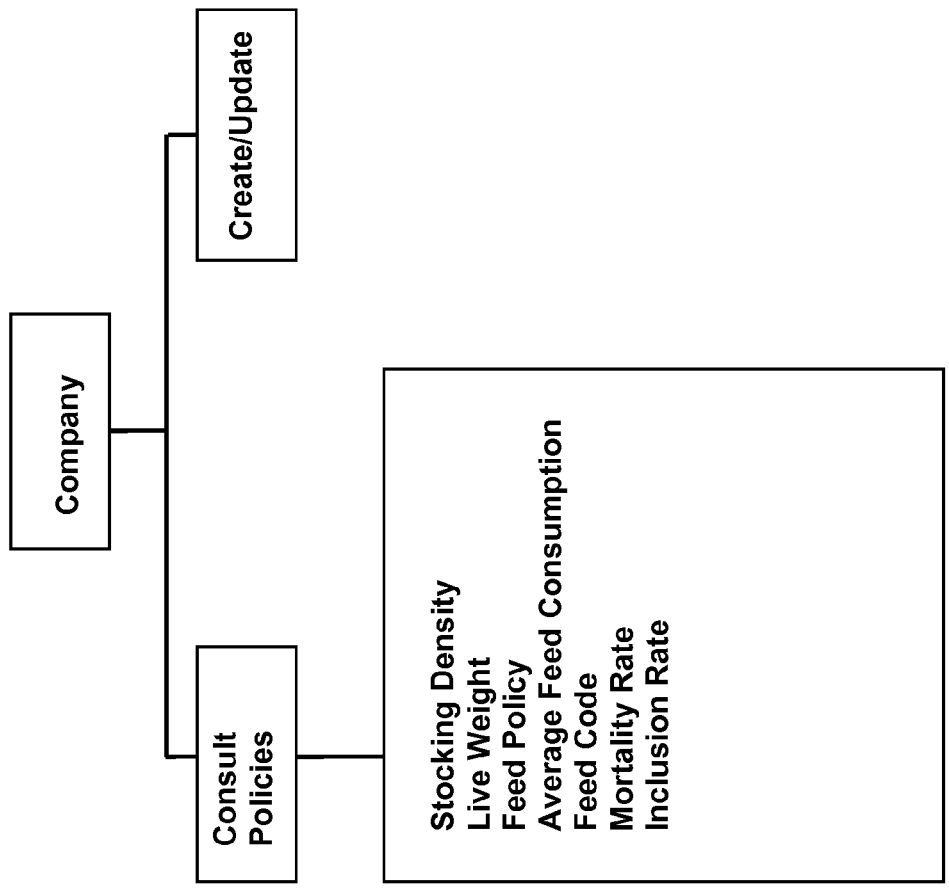

BREED-SPECIFIC HAPLOTYPES FOR POLLED PHENOTYPES IN CATTLE

INCORPORATION BY REFERENCE

This application claims benefit of the U.S. provisional patent application Ser. No. 61/015,521 filed on Dec. 20, 2007.

FEDERAL FUNDING LEGEND

This invention was made with government support under 2003-35205-12825 awarded by USDA/CSREES. Accordingly, the Federal Government has certain rights in this invention.

The foregoing applications, and all documents cited therein or during their prosecution ("appln cited documents") and all documents cited or references in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to methods and systems of identification and management of beef cattle. More specifically, the invention relates to methods and systems relating to identification of single nucleotide polymorphisms (SNPs) and haplotypes associated with the polled phenotype. The invention further relates to methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Animals account for almost 20 percent of the world's food consumption, and animal-based food products are a major source of revenue throughout the world. In the United States alone, beef production is the fourth largest manufacturing industry and accounts for nearly 25 percent of the farm sector cash receipts and seven percent of supermarket sales each year.

Significant improvements in animal performance, efficiency and carcass and meat quality have been made over the years through the application of standard animal breeding and selection techniques. However, such classical animal breeding techniques require several years of genetic evaluation of performance records on individual animals and their relatives and are therefore very expensive. Other efforts have been made to improve productivity and quality through the application of such management practices as the use of feed additives, animal hormonal implants and chemotherapeutics. However, there is significant political and regulatory resistance to the introduction and use of such methodologies. Such methodologies are also non-heritable and need to be applied differently in every production system.

There is a need for methods that allow relatively easy and more efficient selection and breeding of farm animals that have an advantage for a heritable trait of the polled phenotype. The economic significance of the use of genetic markers that are associated with specific economically important traits in livestock through marker-assisted selection cannot therefore be over-emphasized.

The presence of horns within commercial cattle populations increases the chances of injuries, particularly during transportation. Quality defects in the form of bruised carcasses, arising from these injuries, cost the industry millions of dollars every year. Producers and packers ranked bruising as one of their top ten concerns for the fed steer and heifer industry in the National Beef Quality Audit-2000. Bruising was also the number two "quality challenge" of the market cow and bull beef industry. Dehorning cattle provides a recurrent managerial solution to the problem. However, there are negative stress effects to the animal, and concerns that dehorning may be an inhumane treatment.

The polled (hornless) condition in cattle has existed since domestication, and it has been selected by breeders because of its economic importance and ease of management. A single, dominant mutation is believed to cause the polled phenotype, but the causative gene remains unknown.

In 1991, Bricker and Church (Abst. 36th annual meeting of the Genetics Society of Canada [Kingston, Ontario. Jun. 11-14, 1991]) reviewed the co-segregaton of Poll with 1:29 translocation in Charolais cattle and found that Poll is very close to the centromere of chromosome 1. Georges et al., Nature Genetics 4: 206-210 (1993) localized the polled locus to the centromeric end of the bovine chromosome 1. This location was further refined by Brenneman et al., J. Heredity 87:156-161 (1996) to a region proximal to the centromere and 4.9 cM (centimorgan) from microsatellite TGLA49. Using the same population, the interval was further refined to a 1.7 megabase region between IFNAR and SOD1. Recently Drogemuller et al., Mammalian Genome 16: 613-620 (2005) localized the polled locus to a 1.0 megabase region between markers BM6438 and RP42-218J17_MS1 (FIG. 43).

Polymorphisms in candidate genes that show association with specific economically relevant traits (ERT) may be useful markers for marker-assisted selection. It remains advantageous to provide SNPs, so that a more accurate prediction can be made of the Polled phenotype of an animal, and also enable a business method that provides for increased productivity in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

The present invention relates to associations between SNPs and haplotypes of SNPs on bovine chromosome 1 with measures of the Polled phenotype in beef cattle.

The invention encompasses a method for breed-specific sub-grouping of animals according to genotype wherein the animals of each sub-group have similar polymorphisms in the Polled-associated gene(s) that may comprise determining the genotype of each animal to be sub-grouped by determining the presence of single nucleotide polymorphisms in or near the Polled-associated gene(s), and segregating individual animals into sub-groups wherein each animal in a sub-group has similar polymorphisms in the Polled-associated gene(s).

In particular, the invention encompasses a method for identifying an animal having the absence of horns as compared to the general population of animals of that species, comprising subjecting a specimen from the animal to nucleotide sequence analysis to obtain the nucleotide sequence of the animal and determining the presence of a single nucleotide polymorphism in a Polled gene of the animal by using a data storage system that compares the nucleotide sequence of the animal with bovine genotypes, wherein the single nucleotide polymorphism is indicative of the absence of horns.

The invention also encompasses a method for sub-grouping animals according to genotype wherein the animals of each sub-group have a similar genotype in the Polled-associated gene(s) that may comprise determining the genotype of each animal to be sub-grouped by determining the presence of single nucleotide polymorphism(s) of interest in or near the Polled-associated gene(s), and segregating individual animals into sub-groups depending on whether the animals have, or do not have, the single nucleotide polymorphism(s) of interest in or near the Polled-associated genes.

The single nucleotide polymorphism(s) located within the first 3 megabases of bovine chromosome 1 (SEQ ID 43, see FIG. 46, electronic file for sequence listing) may be selected from the group consisting of the following:

SNPs (Bovine Chromosome 1)
1. SNP A1356048G an A to G nucleotide substitution within the context of the following disclosed flanking sequences of: 5'-TATTTCCCTCTT-A/G-AAAAAA-GATAAA-3' (SEQ ID NO: 44).
2. SNP A1872077G an A to G nucleotide substitution within the context of the following disclosed flanking sequences of: 5'-CAAAGTTGTGTC-A/G-GCTTCT-GCTCTC-3' (SEQ ID NO: 45).
3. SNP T1872200C a T to C nucleotide substitution within the context of the following disclosed flanking sequences of: 5'-GGACAGTGGGTT-T/C-TCAT-CAGTTATC-3' (SEQ ID NO: 46).
4. SNP T2101528C a T to C nucleotide substitution within the context of the following disclosed flanking sequences of: 5'-TGTCTCTCTGCT-T/C-CTCTCTCTCCCC-3' (SEQ ID NO: 47).
5. SNP T2214142A a T to A nucleotide substitution within the context of the following disclosed flanking sequences of: 5'-CTTTCCAACTCA-T/A-GGGG-GAAGGATG-3' (SEQ ID NO: 48).
6. SNP T2220054C a T to C nucleotide substitution within the context of the following disclosed flanking sequences of: 5'-TCAACCTGGAGG-T/C-GGGGGTTTGGGG-3' (SEQ ID NO: 49).
7. SNP T2220178A a T to A nucleotide substitution within the context of the following disclosed flanking sequences of: 5'-CACCATTCCAAG-T/A-ACATAGG-TAGGC-3' (SEQ ID NO: 50).
8. SNP C2225310T a C to T nucleotide substitution within the context of the following disclosed flanking sequences of: 5'-AAGGTCTATCTT-C/T-AGGAA-GAGTTGC-3' (SEQ ID NO: 51).
9. SNP G2288436A a G to A nucleotide substitution within the context of the following disclosed flanking sequences of: 5'-TGAACACAGGAG-G/A-GT-GAACGTCTAA-3' (SEQ ID NO: 52).
10. SNP C2332892T a C to T nucleotide substitution within the context of the following disclosed flanking sequences of: 5'-TCTGGCGTTTCG-C/T-GGCCAA-GACACA-3' (SEQ ID NO: 53).
11. SNP G2333140A a G to A nucleotide substitution within the context of the following disclosed flanking sequences of: 5'-ACAAGGATAAAT-G/A-GCAAG-GAAGAAA-3' (SEQ ID NO: 54).
12. SNP C2338338T a C to T nucleotide substitution within the context of the following disclosed flanking sequences of: 5'-AGAGTATTCCAT-C/T-AGGAAAC-CTCAT-3' (SEQ ID NO: 55).
13. SNP T2816109G a T to G nucleotide substitution within the context of the following disclosed flanking sequences of: 5'-GCTTGCCTACAA-T/G-AGAAGA-CATCAG-3' (SEQ ID NO: 56).
14. SNP C2816370G a C to G nucleotide substitution within the context of the following disclosed flanking sequences of: 5'-AATCCCATGAGA-C/G-TGTTGC-CATCAG-3' (SEQ ID NO: 57).
15. SNP HP-1013610 a G to C nucleotide substitution within the context of the following disclosed flanking sequences of: 5'-TCATAAGAATTG-G/C-TACTAC-CTATAC-3' (SEQ ID NO: 58).
16. SNP HP-1352705 a T to A nucleotide substitution within the context of the following disclosed flanking sequences of: 5'-GATACAAACTGT-T/A-ATGTGT-GAGTAG-3' (SEQ ID NO: 59).
17. SNP HP-1352905 a C to G nucleotide substitution within the context of the following disclosed flanking sequences of: 5'-TGAGCATCACCC-C/G-CGG-GAGGGCTCT-3' (SEQ ID NO: 60).
18. SNP HP-1356048 a G to A nucleotide substitution within the context of the following disclosed flanking sequences of: 5'-TATTTCCCTCTT-G/A-AAAAAA-GATAAA-3' (SEQ ID NO: 61).
19. SNP HP-1431709 a G to A nucleotide substitution within the context of the following disclosed flanking sequences of: 5'-TTTTGCAAGGT-G/A-ATCTTGAG-TAAC-3' (SEQ ID NO: 62).
20. SNP HP-1438531 a T to C nucleotide substitution within the context of the following disclosed flanking sequences of: 5'-GAATCTTTTTCC-T/C-CAAATACTTTCT-3' (SEQ ID NO: 63).
21. SNP HP-1731905 a A to G nucleotide substitution within the context of the following disclosed flanking sequences of: 5'-GGAGGGGTATTC-A/G-AGGTGC-TATGAG-3' (SEQ ID NO: 64).
22. SNP HP-1872077 a A to G nucleotide substitution within the context of the following disclosed flanking sequences of: 5'-CAAAGTTGTGTC-A/G-GCTTCT-GCTCTC-3' (SEQ ID NO: 45).
23. SNP HP-1872200 a T to C nucleotide substitution within the context of the following disclosed flanking sequences of: 5'-GGACAGTGGGTT-T/C-TCAT-CAGTTATC-3' (SEQ ID NO: 46).
24. SNP HP-2101528 a C to T nucleotide substitution within the context of the following disclosed flanking sequences of: 5'-CTGTCTCTCTGCT-C/T-CTCTCTCTCCCC-3' (SEQ ID NO: 65).
25. SNP HP-2128551 a T to C nucleotide substitution within the context of the following disclosed flanking sequences of: 5'-TCTCCACTGACT-T/C-CCCCCCTTTCTA-3' (SEQ ID NO: 66).
26. SNP HP-2214142 a A to T nucleotide substitution within the context of the following disclosed flanking sequences of: 5'-CTTTCCAACTCA-A/T-GGGG-GAAGGATG-3' (SEQ ID NO: 67).
27. SNP HP-2220054 a C to T nucleotide substitution within the context of the following disclosed flanking sequences of: 5'-TCAACCTGGAGG-C/T-GGGGGTTTGGGG-3' (SEQ ID NO: 68).
28. SNP HP-2220178 a A to T nucleotide substitution within the context of the following disclosed flanking sequences of: 5'-CACCATTCCAAG-A/T-ACATAGG-TAGGC-3' (SEQ ID NO: 69).
29. SNP HP-2225310 a T to C nucleotide substitution within the context of the following disclosed flanking sequences of: 5'-AAGGTCTATCTT-T/C-AGGAA-GAGTTGC-3' (SEQ ID NO: 70).
30. SNP HP-2288436 a G to A nucleotide substitution within the context of the following disclosed flanking sequences of: 5'-TGAACACAGGAG-G/A-GT-GAACGTCTAA-3' (SEQ ID NO: 52).
31. SNP HP-2332892 a C to T nucleotide substitution within the context of the following disclosed flanking sequences of: 5'-TCTGGCGTTTCG-C/T-GGCCAA-GACACA-3' (SEQ ID NO: 53).
32. SNP HP-2333140 a A to G nucleotide substitution within the context of the following disclosed flanking sequences of: 5'-ACAAGGATAAAT-A/G-GCAAG-GAAGAAA-3' (SEQ ID NO: 71).
33. SNP HP-2338338 a T to C nucleotide substitution within the context of the following disclosed flanking sequences of: 5'-AGAGTATTCCAT-T/C-AGGAAAC-CTCAT-3' (SEQ ID NO: 72).
34. SNP HP-2640799 a T to A nucleotide substitution within the context of the following disclosed flanking sequences of: 5'-CTTTTTCAGAGT-T/A-TGATTAC-CCAGA-3' (SEQ ID NO: 73).
35. SNP HP-2648129 a T to C nucleotide substitution within the context of the following disclosed flanking sequences of: 5'-CTAATAGTTCTT-T/C-ACAGT-GAGCTGA-3' (SEQ ID NO: 74).
36. SNP HP-2650867 a T to A nucleotide substitution within the context of the following disclosed flanking sequences of: 5'-TTTAAACAGTGC-T/A-GGATAT-GCTTTG-3' (SEQ ID NO: 75).
37. SNP HP-2651006 a G to T nucleotide substitution within the context of the following disclosed flanking sequences of: 5'-TCCCCATTCTGA-G/T-CCCCTTTCACCC-3' (SEQ ID NO: 76).
38. SNP HP-2657651 a G to C nucleotide substitution within the context of the following disclosed flanking sequences of: 5'-TGGTTAAACCAC-G/C-CCT-TCGGGTTAT-3' (SEQ ID NO: 77).
39. SNP HP-2676311 a T to C nucleotide substitution within the context of the following disclosed flanking sequences of: 5'-CTCTTGCTCTTC-T/C-CATACAC-CGCAA-3' (SEQ ID NO: 78).
40. SNP HP-2816109 a T to G nucleotide substitution within the context of the following disclosed flanking sequences of: 5'-GCTTGCCTACAA-T/G-AGAAGA-CATCAG-3' (SEQ ID NO: 56).
41. SNP HP-2816370 a C to G nucleotide substitution within the context of the following disclosed flanking sequences of: 5'-AATCCCATGAGA-C/G-TGTTGC-CATCAG-3' (SEQ ID NO: 57).
42. SNP HP-2820224 a T to G nucleotide substitution within the context of the following disclosed flanking sequences of: 5'-GCCAATTTTTC-T/G-CAAGTC-CAACAA-3' (SEQ ID NO: 79).

The invention further relates to a method for sub-grouping animals according to genotype wherein the animals of each sub-group have similar haplotypes in the Polled-associated gene(s) that may comprise determining the genotype of each animal to be sub-grouped by determining the presence of any of the above SNPs, and segregating individual animals into sub-groups depending on whether the animals have, or do not have, any of the above SNPs in or near the Polled-associated genes.

The invention also relates to a method for identifying an animal having a desirable phenotype as compared to the general population of animals of that species, which may comprise determining the presence of single nucleotide polymorphisms in or near the Polled-associated genes of the animal, wherein the presence of the SNPs are indicative of a desirable phenotype.

In an advantageous embodiment, the animal may be a bovine. In another advantageous embodiment, the Polled-associated genes may be bovine Polled-associated genes.

The invention also encompasses computer-assisted methods and systems for improving the production efficiency for livestock using multiple data, and in particular the genotype of the animals as it relates to Polled-associated SNPs. Methods of the invention encompass obtaining a genetic sample from each animal in a herd of livestock, determining the genotype of each animal with respect to specific quality traits as defined by a panel of at least two single nucleotide polymorphisms (SNPs), grouping animals with like genotypes, and optionally, further sub-grouping animals based on like phenotypes and haplotypes. Methods of the invention may also encompass obtaining and maintaining data relating to the animals or to herds, their husbandry conditions, health and veterinary care and condition, genetic history or parentage, and providing those data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within or near the Polled-associated genes related to production and associating those data with other data about the animal or its herd, and maintaining those data in ways that are accessible. Another aspect of the invention encompasses a computer-assisted method for predicting which livestock animals possess a biological difference in Polled, and which may include the steps of using a computer system, e.g., a programmed computer comprising a processor, a data storage system, an input device and an output device, the steps of: (a) inputting into the programmed computer through the input device data that include a genotype of an animal as it relates to any one of the Polled-associated SNPs described herein, (b) correlating production efficiency or carcass merit predicted by the Polled-associated genotypes using the processor and the data storage system and (c) outputting to the output device the predicted production efficiency or carcass merit correlated to the Polled-associated genotypes, thereby predicting which livestock animals possess desirable characteristics for animal handling and carcass merit, including freedom from bruising.

Yet another aspect of the invention relates to a method of doing business for managing livestock comprising providing to a user a computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein such physical characteristics as increased potential for carcass merit due to freedom from bruising are associated with the Polled genotype and haplotypes.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of examples, but not intended to limit the invention solely to the specific embodiments described, may best be understood in conjunction with the accompanying drawings, in which:

FIG. 1 depicts 500 bp of nucleic acid sequence (250 bp on either side) of SNP A1356048G (SEQ ID NO: 1) in build Btau3.0 of the bovine genome sequence.

FIG. 2 depicts 500 bp of nucleic acid sequence (250 bp on either side) of SNP A1872077G (SEQ ID NO: 2) in build Btau3.0 of the bovine genome sequence.

FIG. 3 depicts 500 bp of nucleic acid sequence (250 bp on either side) of SNP T1872200C (SEQ ID NO: 3) in build Btau3.0 of the bovine genome sequence.

FIG. 4 depicts 500 bp of nucleic acid sequence (250 bp on either side) of SNP T2101528C (SEQ ID NO: 4) in build Btau3.0 of the bovine genome sequence.

FIG. 5 depicts 500 bp of nucleic acid sequence (250 bp on either side) of SNP T2214142A (SEQ ID NO: 5) in build Btau3.0 of the bovine genome sequence.

FIG. 6 depicts 500 bp of nucleic acid sequence (250 bp on either side) of SNP T2220054C (SEQ ID NO: 6) in build Btau3.0 of the bovine genome sequence.

FIG. 7 depicts 500 bp of nucleic acid sequence (250 bp on either side) of SNP T2220178A (SEQ ID NO: 7) in build Btau3.0 of the bovine genome sequence.

FIG. 8 depicts 500 bp of nucleic acid sequence (250 bp on either side) of SNP C2225310T (SEQ ID NO: 8) in build Btau3.0 of the bovine genome sequence.

FIG. 9 depicts 500 bp of nucleic acid sequence (250 bp on either side) of SNP G2288436A (SEQ ID NO: 9) in build Btau3.0 of the bovine genome sequence.

FIG. 10 depicts 500 bp of nucleic acid sequence (250 bp on either side) of SNP C2332892T (SEQ ID NO: 10) in build Btau3.0 of the bovine genome sequence.

FIG. 11 depicts 500 bp of nucleic acid sequence (250 bp on either side) of SNP G2333140A (SEQ ID NO: 1) in build Btau3.0 of the bovine genome sequence.

FIG. 12 depicts 500 bp of nucleic acid sequence (250 bp on either side) of SNP C2338338T (SEQ ID NO: 12) in build Btau3.0 of the bovine genome sequence.

FIG. 13 depicts 500 bp of nucleic acid sequence (250 bp on either side) of SNP T2816109G (SEQ ID NO: 13) in build Btau3.0 of the bovine genome sequence.

FIG. 14 depicts 500 bp of nucleic acid sequence (250 bp on either side) of SNP C2816370G (SEQ ID NO: 14) in build Btau3.0 of the bovine genome sequence.

FIG. 15 depicts 500 bp of nucleic acid sequence (250 bp on either side) of SNP HP-1013610 (SEQ ID NO: 15) in build Btau3.0 of the bovine genome sequence.

FIG. 16 depicts 500 bp of nucleic acid sequence (250 bp on either side) of SNP HP-1352705 (SEQ ID NO: 16) in build Btau3.0 of the bovine genome sequence.

FIG. 17 depicts 500 bp of nucleic acid sequence (250 bp on either side) of SNP HP-1352905 (SEQ ID NO: 17) in build Btau3.0 of the bovine genome sequence.

FIG. 18 depicts 500 bp of nucleic acid sequence (250 bp on either side) of SNP HP-1356048 (SEQ ID NO: 18) in build Btau3.0 of the bovine genome sequence.

FIG. 19 depicts 500 bp of nucleic acid sequence (250 bp on either side) of SNP HP-1431709 (SEQ ID NO: 19) in build Btau3.0 of the bovine genome sequence.

FIG. 20 depicts 500 bp of nucleic acid sequence (250 bp on either side) of SNP HP-1438531 (SEQ ID NO: 20) in build Btau3.0 of the bovine genome sequence.

FIG. 21 depicts 500 bp of nucleic acid sequence (250 bp on either side) of SNP HP-1731905 (SEQ ID NO: 21) in build Btau3.0 of the bovine genome sequence.

FIG. 22 depicts 500 bp of nucleic acid sequence (250 bp on either side) of SNP HP-1872077 (SEQ ID NO: 22) in build Btau3.0 of the bovine genome sequence.

FIG. 23 depicts 500 bp of nucleic acid sequence (250 bp on either side) of SNP HP-1872200 (SEQ ID NO: 23) in build Btau3.0 of the bovine genome sequence.

FIG. 24 depicts 500 bp of nucleic acid sequence (250 bp on either side) of SNP HP-2101528 (SEQ ID NO: 24) in build Btau3.0 of the bovine genome sequence.

FIG. 25 depicts 500 bp of nucleic acid sequence (250 bp on either side) of SNP HP-2128551 (SEQ ID NO: 25) in build Btau3.0 of the bovine genome sequence.

FIG. 26 depicts 500 bp of nucleic acid sequence (250 bp on either side) of SNP HP-2214142 (SEQ ID NO: 26) in build Btau3.0 of the bovine genome sequence.

FIG. 27 depicts 500 bp of nucleic acid sequence (250 bp on either side) of SNP HP-2220054 (SEQ ID NO: 27) in build Btau3.0 of the bovine genome sequence.

FIG. 28 depicts 500 bp of nucleic acid sequence (250 bp on either side) of SNP HP-2220178 (SEQ ID NO: 28) in build Btau3.0 of the bovine genome sequence.

FIG. 29 depicts 500 bp of nucleic acid sequence (250 bp on either side) of SNP HP-2225310 (SEQ ID NO: 29) in build Btau3.0 of the bovine genome sequence.

FIG. 30 depicts 500 bp of nucleic acid sequence (250 bp on either side) of SNP HP-2288436 (SEQ ID NO: 30) in build Btau3.0 of the bovine genome sequence.

FIG. 31 depicts 500 bp of nucleic acid sequence (250 bp on either side) of SNP HP-2332892 (SEQ ID NO: 31) in build Btau3.0 of the bovine genome sequence.

FIG. 32 depicts 500 bp of nucleic acid sequence (250 bp on either side) of SNP HP-2333140 (SEQ ID NO: 32) in build Btau3.0 of the bovine genome sequence.

FIG. 33 depicts 500 bp of nucleic acid sequence (250 bp on either side) of SNP HP-2338338 (SEQ ID NO: 33) in build Btau3.0 of the bovine genome sequence.

FIG. 34 depicts 500 bp of nucleic acid sequence (250 bp on either side) of SNP HP-2640799 (SEQ ID NO: 34) in build Btau3.0 of the bovine genome sequence.

FIG. 35 depicts 500 bp of nucleic acid sequence (250 bp on either side) of SNP HP-2648129 (SEQ ID NO: 35) in build Btau3.0 of the bovine genome sequence.

FIG. 36 depicts 500 bp of nucleic acid sequence (250 bp on either side) of SNP HP-2650867 (SEQ ID NO: 36) in build Btau3.0 of the bovine genome sequence.

FIG. 37 depicts 500 bp of nucleic acid sequence (250 bp on either side) of SNP HP-2651006 (SEQ ID NO: 37) in build Btau3.0 of the bovine genome sequence.

FIG. 38 depicts 500 bp of nucleic acid sequence (250 bp on either side) of SNP HP-2657651 (SEQ ID NO: 38) in build Btau3.0 of the bovine genome sequence.

FIG. 39 depicts 500 bp of nucleic acid sequence (250 bp on either side) of SNP HP-2676311 (SEQ ID NO: 39) in build Btau3.0 of the bovine genome sequence.

FIG. 40 depicts 500 bp of nucleic acid sequence (250 bp on either side) of SNP HP-2816109 (SEQ ID NO: 40) in build Btau3.0 of the bovine genome sequence.

FIG. 41 depicts 500 bp of nucleic acid sequence (250 bp on either side) of SNP HP-2816370 (SEQ ID NO: 41) in build Btau3.0 of the bovine genome sequence.

FIG. 42 depicts 500 bp of nucleic acid sequence (250 bp on either side) of SNP HP-2820224 (SEQ ID NO: 42) in build Btau3.0 of the bovine genome sequence.

FIG. 43 illustrates a genetic linkage map for Poll on Bovine chromosome 1.

FIG. 44 lists species-specific bovine Polled minor allele frequencies.

FIG. 45 depicts the mode of Poll Inheritance as defined by Long and Gregory, J. Heredity 69: 395-400 (1978). In this illustration, the predicted phenotypes of Horned (hollow, bony growths that are fused to the skull), Scurred (loose "cartilaginous" growths), and Polled (no growth) inheritance are shown relative to genotypes.

FIG. 46 depicts the first 3 Mb (bases 1 thru 3,000,000) of the Sequence of Bos taurus Chromosome 1 build Btau3.0 (SEQ ID NO. 43). See electronic compact disk sequence listing. File name: Btaurus Chm 1 seq.txt.

FIG. 47 presents a comparison of horn/poll marker coordinates in successive releases of the bovine genome sequence.

FIG. 50C illustrates the flow of events through the subroutines related to data entry concerning data specific to a company.

DETAILED DESCRIPTION

Figure 48:
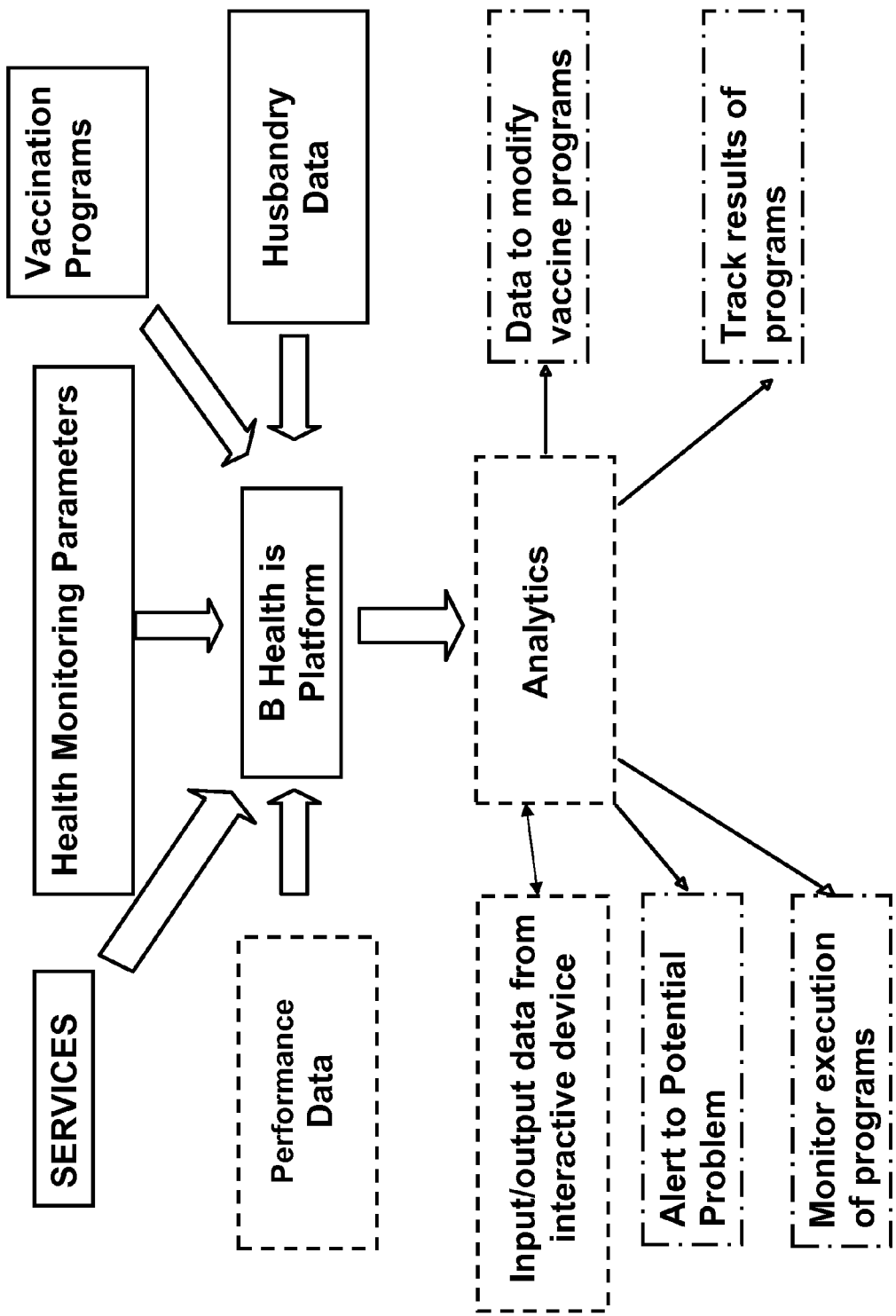
FIG. 48 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, real-time PCR, etc., may be used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3 SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to a locatable region of genomic sequence, corresponding to a unit of inheritance, which is associated with regulatory regions, transcribed regions and/or other functional sequence regions. The physical development and phenotype of organisms can be thought of as a product of genes interacting with each other and with the environment. A concise definition of "gene" taking into account complex patterns of regulation and transcription, genic conservation and non-coding RNA genes, has been proposed by Gerstein et al. (Genome Research 17 (6), 669-681, 2007) "A gene is a union of genomic sequences encoding a coherent set of potentially overlapping functional products". In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Sequence identity" refers to the percent identity between two polynucleotide or two polypeptide moieties. Genes that share a high sequence identity or similarity support the hypothesis that they share a common ancestor and are therefore homologous. Sequence homology may also indicate common function. Two DNA, or two polypeptide sequences are similar to each other and may be homologous when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, Sequence identity also refers to sequences showing complete identity (100% sequence identity) to the specified DNA or polypeptide sequence.

Percent identity can be determined by hybridization of polynucleotides under conditions that form stable duplexes between similar regions, followed by digestion with single-stranded-specific nuclease(s), and size determination of the digested fragments. DNA sequences that are homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in or near a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat or remain free from bruising due to trauma from horns during the process of handling. Physical characteristics include, but are not limited to, marbled, tender or lean meats and horned or polled status. The terms may be used interchangeably.

Statistical associations between individual SNP or SNP haplotypes and the phenotype of interest can be determined in a case-control study by utilizing the algorithms in computer software such as in PHASE2.1.1 (M. Stephens and P. Donnelly, Am. J. Human Genet. 73: 1162-1169, 2003) and Haploview (J. C. Barrett et al., Bioinformatics 21: 263-265, 2005).

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and include, but are not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian As used herein, the term "data storage system" refers to any person, object or system that compares the nucleotide sequence of the animal with other genotypes. By example and without limitation, the term may define, individually or collectively, the person or machine analyzing the samples, the containers holding the nucleotide samples, the packaging used for transporting the samples, and the like.

The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene(s) of interest is bovine Polled, the bovine Polled nucleotide sequence can be selected from, but is not limited to, the sequences corresponding to SEQ ID NO 1 through SEQ ID NO 42, or fragments thereof or a region of the bovine genome that comprises said sequence(s).

The single nucleotide polymorphism(s) of interest may be selected from the group comprising the nucleotide substitutions defined in SEQ ID NO 1 through SEQ ID NO 42 (FIG. 1 through FIG. 42).

The SNPs advantageous in the present invention are associated with certain economically valuable and heritable traits relating to quality in bovines. Therefore, it is an object of the present invention to determine the genotype of a given animal of interest as defined by the nucleotide substitutions defined in SEQ ID NO 1 through SEQ ID NO 42 (FIG. 1 through FIG. 42) according to the present invention. It is also contemplated that the genotype of the animal(s) may be defined by additional SNPs within the Polled gene(s) or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits to be identified based on the presence of SNPs in their genomes and particularly with SNPs located within the Polled genes. The methods further allow, by computer-assisted methods of the invention, to correlate SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 μl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of the gene(s) of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the Polled gene(s), advantageously of the region encompassing a Polled SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or similarity with a Polled gene or probes or primers derived therefrom such as at least 75% identity or similarity, preferably at least 80% identity or similarity, more preferably at least 85% identity or similarity such as at least 90% identity or similarity, more preferably at least 95% identity or similarity such as at least 97% identity or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity", for instance, with respect to a nucleotide sequence, is intended to indicate a quantitative measure of factual identity between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in or near a Polled gene which are unique to that location. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3$H, $^{125}$I, $^{35}$S, $^{14}$C, $^{32}$P, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% sequence identity with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^{3}H$, $^{125}I$, $^{35}S$, $^{14}C$, $^{32}P$, etc.), enzymes (e.g. horseradish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and MacBeath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved production, meat quality and yield, and meat tenderness. Continuous selection and breeding of animals, such as livestock, that are at least heterozygous and advantageously homozygous for desirable alleles of the Polled gene polymorphic sites associated with economically relevant production traits, would lead to a breed, line, or population having higher numbers of offspring with economically relevant production traits such as polled. Animals with the polled condition are advantageous for animal and human safety during handling, and for carcass quality due to reduced bruising. Thus, the Polled-associated SNPs of the present invention can be used as a selection tool.

Desirable phenotypes include, but are not limited to production, feed intake, growth rate, body weight, carcass merit and composition, polled status, and milk yield. Specific carcass traits with desirable phenotypes include, but are not limited to, additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF %, %), marbling score (MBS, 10 to 99), marbling score divided by days on feed (MBS/DOF), quality grade, less than or equal to select versus greater than or equal to choice (QG, <Se vs, >Ch), ribeye area (REA, in$^2$), ribeye area per hundred weight HCW (REA/cwt HCW, in$^2$/100 lb hot carcass weight (HCW) and subcutaneous fat depth (SFD) or freedom from bruising.

One aspect of the present invention provides for grouping animals and methods for managing livestock production comprising grouping livestock animals such as cattle according the genotype as defined by panels of SNPs, each panel comprising at least one SNP, one or more of which are in or near the Polled-associated gene(s) of the present invention. Other SNPs that may be included in panels of SNPs include, but not limited to, SNPs found in the calpain gene calpastatin gene, FGF8 gene, DECR 1 gene, GHR gene, TFAM gene, CRH gene, FABP4 gene, ghrelin gene, leptin gene, NPY gene, and/or the UCP2 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, feed intake, carcass/meat quality and milk production. The present invention provides methods of screening livestock to determine those more likely to develop a Polled condition by identifying the presence or absence of one or more gene polymorphisms correlated with the Polled phenotype.

As described above, and in the Examples, the phenotypic trait with which the SNPs of the present invention may be associated is the presence or absence of horns. The phenotypic and genetic trait can be tested using the methods described in the Examples, or using any suitable methods known in the art. Using the methods of the invention, a farmer, or feedlot operator, or the like, can group cattle according to each animal's genetic propensity for Polled, as determined by SNP genotype. The cattle are tested to determine homozygosity or heterozygosity with respect to the SNP alleles of the gene.

The individual genotypic data derived from a panel or panels of SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data have or have not been associated with other data, the data are stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or sub-grouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data include, but are not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, detection of circulating hormone leves (eg. leptin), bovine spongiform encephalopathy (BSE) diagnosis, brucellosis vaccination, FMD (foot and mouth disease) vaccination, BVD (bovine viral diarrhea) vaccination, Sure Health pre-conditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are Polled-associated sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the Polled-associated sequences described herein.

Another embodiment of the invention is an oligonucleotide that specifically hybridizes under high stringency conditions to any one of the polymorphic sites of the Polled-associated gene(s), wherein the oligonucleotide is between about 18 nucleotides and about 50 nucleotides.

In another embodiment of the invention, the oligonucleotide comprises a central nucleotide specifically hybridizing with a Polled-associated gene(s) polymorphic site of the portion of the nucleic acid molecule.

Another aspect of the invention is a method of identifying a Polled-associated polymorphisms in a nucleic acid sample comprising isolating a nucleic acid molecule encoding Polled-associated genes or a fragment thereof and determining the nucleotide at the polymorphic site.

Another aspect of the invention is a method of screening cattle to determine those bovines more likely to exhibit a biological difference in production quality comprising the steps of obtaining a sample of genetic material from a bovine; and assaying for the presence of a genotype in the bovine which is associated with production quality, the genotype characterized by polymorphisms in the Polled-associated genes.

In other embodiments of this aspect of the invention, the step of assaying is selected from the group consisting of: restriction fragment length polymorphism (RFLP) analysis, minisequencing, MALDI-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of or near the Polled-associated gene or a portion thereof that contains the polymorphism. In other embodiments of the invention, the amplification may include the step of selecting a forward and a reverse sequence primer capable of amplifying a region of the Polled-associated gene.

Another aspect of the invention is a computer-assisted method for predicting which livestock animals possess a biological difference in production quality comprising: using a computer system, e.g., a programmed computer comprising a processor, a data storage system, an input device and an output device, the steps of: (a) inputting into the programmed computer through the input device data comprising a Polled-associated genotype of an animal, (b) correlating production quality predicted by the Polled-associated genotype using the processor and the data storage system and (c) outputting to the output device the production quality correlated to the Polled-associated genotype, thereby predicting which livestock animals possess a particular quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention described herein is a SNP-based test in which data have been generated on a breed-by-breed basis and thus identifying breed-specific Polled haplotypes. There have been no assumptions regarding the origin of the Polled mutation (ie. whether there was a single or multiple mutation events), but it has been assumed that the specific mutation lies within a 1.7 Mb region near the centromere on bovine chromosome 1 in all breeds of interest.

The invention will now be further described by way of the following non-limiting examples.

EXAMPLES

Example 1

This Example provides DNA loci, genetic polymorphisms and significant associations with Polled-associated genes. A linkage map of Bovine Chromosome 1 (BTA1) is shown in FIG. 43 which shows localization of Poll to the region between IFNAR and SOD. Drogemuller et al. (2005) have localized Poll between BM6438 and RP42-218J17_MS1.

The Polled mutation lies within a 1.7 Mb region on bovine chromosome 1. In this example, we identified SNPs that spanned this 1.7 Mb interval, by mining the bovine genome sequence, by comparison of bacterial artificial chromosome (BAC) end sequences to the bovine genome sequence or from in-house sequence data. The relative position of SNPs was determined based on a physical map of the interval. SNPs are named based on their position in build 3.0 of the bovine genome sequence. For reference, FIG. 47 provides a comparison of horn/poll marker coordinates in successive releases of the bovine genome sequence. A SNPlex assay (Applied Biosystems) of 44 SNP probes was developed and used 42 SNPs in the association study. FIGS. 1-42 list the 42 SNPs and 250 bp of flanking sequence on either side of the specific SNP.

Example 2

Breeds of interest in this study were Limousin, Hereford, Angus, Red Angus, Simmental, Gelbvieh, Charolais, Brahman, Jersey and Holstein. We identified animals based on phenotypic information recorded in semen catalogs or at breed association websites. To ensure animals used for discovery were as unrelated as possible we constructed 5-generation pedigrees and used those animals with relationship coefficients <0.0625. In FIG. 44 a compilation of breed-specific Minor Allele Frequencies is presented.

For Limousin, we used 16 unrelated animals (32 chromosomes) for the discovery phase. A case/control study was performed with horned animals coded as controls and polled animals as case. Haplotypes were reconstructed for the 14 SNPs using PHASE software and differences in the frequencies of case vs. control haplotypes were investigated. Significance of the association of particular haplotypes with horned vs. polled phenotypes was also investigated using Haploview software. Data were permutated 10,000 times to establish empirical significance thresholds. Three SNPs (A1872077G, G2288436A, C2332892T) were sufficient to distinguish horned, heterozygous polled or homozygous polled individuals based on phased haplotype data. T1872200C is in complete disequilibrium with A1872077G and could be used instead. Two additional SNPs (T2101528C, T2214142A) were needed to correctly diagnose these phenotypes based on genotypes instead of haplotypes. T2220054C, T2220178 and C2225310T are in complete disequilibrium with T2214142A and could be used instead. The haplotypes for the 5 SNP markers for Limousin are listed in Table 1 and the P-values associated with individual markers or haplotypes are in Table 2.

Example 3

A blind test was performed to investigate the accuracy of predictions from the 5 marker haplotypes. Twenty five Limousin DNA samples were extracted and coded to keep them blind from the individual performing analysis. A SNPlex assay was performed and the resultant genotypes were phased as previously. Both alleles could be assigned for 23 individuals. A haplotype that had not previously been observed was seen in 2 individuals, so these could not be assigned blind. For the remaining 23 individuals, the predicted phenotypes matched the breed association records of phenotypes with 100% accuracy. A final check of the significance of the associations was performed by creating a dataset combining all individuals (original discovery set and blind-tested). After 10,000 permutations of the data, the best permutation chi-square was 19.212 while the best observed chi-square was 28.293 for SNP C2332892T. This corresponds to a P-value of $1 \times 10^{-7}$.

Example 4

For Hereford, 32 unrelated animals (64 chromosomes) were used for the discovery phase. As in the example for Limousin (Example 2), a case/control study was performed after reconstructing the haplotypes for 28 SNPs using PHASE software. Five SNPs (A1356048G, T2101528C, T2214142A, G2333140A, and T2816109G) were sufficient to distinguish horned, heterozygous polled or homozygous polled individuals based on phased haplotype data. As for the Limousin data, T2220054C, T2220178 and C2225310T are in complete disequilibrium with T2214142A and could be used instead. C2338338T is in complete linkage disequilibrium with G2333140A and C2816370G is in complete linkage disequilibrium with T2816109G. After 10,000 permutations of the data, the best permutation chi-square was 23.863 while the best observed chi-square was 32.789 for SNP T2816109C. This corresponds to a P-value of $1 \times 10^{-8}$ (Table 3).

Example 5

Haplotypes associated with the polled phenotype in the Angus and Red Angus breeds were identified and characterized (Table 4). A predictive test for the horned or polled phenotypes in Gelbvieh was also developed (Table 5) and has gone through a blind testing phase to verify accuracy. The polled phenotypes in Gelbvieh were derived from the Angus and/or Red Angus breeds. This is a predictive test and at present is suitable for purebred cattle.

For Angus and Red Angus, 56 unrelated animals (112 chromosomes) were used in a combined analysis. Because all individuals in these breeds are polled, haplotypes were simply reconstructed for the 28 SNP using PHASE software. These haplotypes are presented in Table 4. It is expected that in breeds that were originally horned, the polled was often introgressed from Angus and so polled haplotypes in those breeds are derived from Angus haplotypes.

For Gelbvieh, 36 unrelated animals (72 chromosomes) were used for the discovery phase. A case/control study was performed with horned animals (n=7) coded as controls and polled animals (n=29) as case. Haplotypes were reconstructed for the 23 polymorphic SNP in Gelbvieh using PHASE software and differences in the frequencies of case vs. control haplotypes were investigated. Significance of the association of particular haplotypes with horned vs. polled phenotypes was also investigated using Haploview software. Data were permutated 10,000 times to establish empirical significance thresholds. Six SNP from the Limousin and Hereford assays (A1356048G, T2220054C, G2288436A, C2332892T, G2333140A, T2816109G, C2816370G) were sufficient to correctly distinguish all but one of the observed horned or polled haplotypes. C2816370G is in complete disequilibrium with T2816109G and could be used instead. Two additional SNP (T2128551C, T2650867A) were needed to correctly distinguish horned and polled individuals carrying the remaining 6-marker haplotype. The haplotypes for the 8 SNP markers for Gelbvieh are listed in Table 5.

Example 6

Haplotypes associated with the polled phenotype in the Charolais, Shorthorn and Jersey breeds were identified and characterized (Table 6). This is a predictive test and is suitable for purebred cattle. We identified animals based on phenotypic information recorded in semen catalogs or at breed association websites. To ensure animals used for discovery were as unrelated as possible we constructed 5-generation pedigrees and used those animals with relationship coefficients <0.0625. Subsequently we obtained progeny records by type of dam (horned, polled or scurred) to verify the phenotype of the study animals.

For Charolais, 49 unrelated animals (98 chromosomes) were used for the discovery phase. A case/control study was performed with the horned animals (n=7) coded as controls and polled animals (n=42) as case. Haplotypes were reconstructed for the 23 polymorphic SNP in Charolais using PHASE software and differences in the frequencies of case vs. control haplotypes were investigated. Significance of the association of particular haplotypes with horned vs. polled phenotypes was also investigated using Haploview software. Data were permutated 10,000 times to establish empirical significance thresholds. Four SNP from the Limousin and Hereford assays (A1872077G, T2214142A, C2332892T, T2816109G), plus two additional SNP (G1013610C, A1731905G) were sufficient to correctly distinguish all of the observed horned or polled haplotypes. The haplotypes for the 8 SNP markers for Charolais are listed in Table 6.

For Shorthorn, 41 unrelated animals (82 chromosomes) were used for the discovery phase. A case/control study was performed with horned animals (n=14) coded as controls and polled animals (n=27) as case. Haplotypes were reconstructed for the 24 polymorphic SNP in Shorthorn using PHASE and Haploview software as for Charolais. Six SNP from the Limousin and Hereford assays (T2101528C, T2214142A, G2288436A, C2332892T, G2333140A, T2816109G), one SNP from the Gelbvieh assay (T2128551C) and one additional SNP that was also used for Charolais (A1731905G) were sufficient to correctly distinguish all but one of the observed horned or polled haplotypes. The haplotypes for the 8 SNP markers for Shorthorn are listed in Table 7.

For Jersey, 24 animals (48 chromosomes) were used for the discovery phase and performed a case/control study as for the beef breeds with the horned animals (n=10) coded as controls and polled animals (n=14) as case. Haplotypes were reconstructed for 20 polymorphic SNP with PHASE and Haploview software as previously described. Four SNP from the Limousin and Hereford assays (A1356048G, T2101528C, G2288436A, G2333140A) were sufficient to correctly distinguish each of the horned and polled haplotypes observed. The haplotypes for the 4 SNP markers for Jersey are listed in Table 8.

TABLE 1

Limousin haplotypes for markers A1872077G, T2101528C, T2214142A, G2288436A, C2332892T

| Haplotype | Phenotype |
|---|---|
| GTTAT | horn |
| GTTAC | horn |
| GTTGT | horn |
| GTTGC | horn |
| GTAAT | horn |
| GTAAC | horn |
| GTAGT | horn |
| GTAGC | horn |
| GCTAT | horn |
| GCTAC | horn |
| GCTGT | horn |
| GCTGC | horn |

TABLE 1-continued

Limousin haplotypes for markers A1872077G, T2101528C, T2214142A, G2288436A, C2332892T

| Haplotype | Phenotype |
|---|---|
| GCAAT | horn |
| GCAAC | horn |
| GCAGT | horn |
| GCAGC | horn |
| ATTAT | horn |
| ATTAC | inconclusive |
| ATTGT | horn |
| ATAAT | horn |
| ATAAC | horn |
| ATAGT | horn |
| ACTAT | horn |
| ACTAC | horn |
| ACTGT | horn |
| ACAAT | horn |
| ACAAC | horn |
| ACAGT | horn |
| ACAGC | poll |
| ATTGC | poll |
| ACTGC | poll |
| ATAGC | poll |

TABLE 2

Markers associated with detection of polled in Limousin

| # | Name | Associated Allele | Case | Control Ratios | Chi Square | P Value |
|---|---|---|---|---|---|---|
| 1 | 1872077 | A | 45:9 | 9:19 | 21.488 | 3.5608E−6 |
| 2 | 1872200 | T | 45:9 | 9:19 | 21.488 | 3.5608E−6 |
| 3 | 2101528 | C | 15:39 | 5:23 | 0.984 | 0.3212 |
| 4 | 2214142 | A | 14:40 | 3:25 | 2.596 | 0.1071 |
| 5 | 2220054 | C | 14:40 | 3:25 | 2.596 | 0.1071 |
| 6 | 2220178 | A | 14:40 | 3:25 | 2.596 | 0.1071 |
| 7 | 2225310 | T | 14:40 | 3:25 | 2.596 | 0.1071 |
| 8 | 2288436 | G | 40:14 | 4:24 | 26.507 | 2.6257E−7 |
| 9 | 2332892 | C | 40:13 | 4.24 | 28.293 | 1.0427E−7 |

| Haplotype | Frequency | Case | Control Ratios | Chi Square | P Value |
|---|---|---|---|---|---|
| Block 1 (1872077, 1872200) | | | | | |
| AT | 0.659 | 45.0:9.0 | 9.0:19.0 | 21.488 | 3.5608E−6 |
| GC | 0.341 | 9.0:45.0 | 19.0:9.0 | 21.488 | 3.5608E−6 |
| Block 2 (2214142, 2220054, 2220178, 2225310, 2288436) | | | | | |
| TTTCA | 0.463 | 14.0:40.0 | 24.0:4.0 | 26.507 | 2.6257E−7 |
| TTTCG | 0.329 | 26.0:28.0 | 1.0:27.0 | 16.590 | 4.6387E−5 |
| ACATG | 0.207 | 14.0:40.0 | 3.0:25.0 | 2.596 | 0.1071 |

TABLE 3

Markers associated with detection of Polled in Hereford

| # | Name | Associated Allele | Case | Control Ratios | Chi Square | P Value |
|---|------|-------------------|------|----------------|------------|---------|
| 1 | 1356048 | G | 30:6 | 10:16 | 13.278 | 3.0E−4 |
| 3 | 2101528 | T | 21:12 | 6:22 | 10.259 | 0.0014 |
| 4 | 2214142 | T | 32:2 | 13:15 | 17.547 | 2.8028E−5 |
| 5 | 2220054 | T | 34:2 | 13:15 | 18.615 | 1.5996E−5 |
| 6 | 2220178 | T | 34:2 | 13:15 | 18.615 | 1.5996E−5 |
| 7 | 2225310 | C | 34:2 | 13:15 | 18.615 | 1.5996E−5 |
| 8 | 2333140 | G | 34:2 | 13:15 | 14.663 | 1.0E−4 |
| 9 | 2338338 | C | 34:2 | 14:12 | 14.234 | 2.0E−4 |
| 10 | 2816109 | T | 31:5 | 24:32 | 1.027 | 2.0E−8 |
| 11 | 2806370 | C | 31:5 | 22:30 | 2.983 | 1.0E−8 |

Block 1 (2214142, 2220054, 2220178, 2225310)

| Haplotype | Frequency | Case | Control Ratios | Chi Square | P Value |
|-----------|-----------|------|----------------|------------|---------|
| TTTC | 0.734 | 34.0:2.0 | 13.0:15.0 | 18.615 | 1.5996E−5 |
| ACAT | 0.266 | 2.0:34.0 | 15.0:13.0 | 18.615 | 1.5996E−5 |

Block 2 (2333140, 2338338)

| Haplotype | Frequency | Case | Control Ratios | Chi Square | P Value |
|-----------|-----------|------|----------------|------------|---------|
| GC | 0.766 | 34.0:2.0 | 15.0:13.0 | 14.663 | 1.0E−4 |
| AT | 0.234 | 2.0:34.0 | 13.0:15.0 | 14.663 | 1.0E−4 |

Block 3 (2816109, 2816370)

| Haplotype | Frequency | Case | Control Ratios | Chi Square | P Value |
|-----------|-----------|------|----------------|------------|---------|
| TC | 0.547 | 31.0:5.0 | 4.0:24.0 | 32.789 | 1.0272E |
| GG | 0.453 | 5.0:31.0 | 24.0:4.0 | 32.789 | 1.0272E |

Hereford haplotypes for markers A1356048G, T2101528C, T2214142A, G2333140A, T2816109G

| Haplotype | Phenotype | Score |
|-----------|-----------|-------|
| ACAAG | Horned | H |
| ACAGG | Horned | H |
| ACAGT | Horned | H |
| ACTGG | Horned | H |
| ACTGT | Horned | H |
| ATAGT | Horned | H |
| ATTAT | Inconsistent | I |
| ATTGG | Horned | H |
| ATTGT | Horned | H |
| GCAAG | Horned | H |
| GCAAT | Horned | H |
| GCAGG | Horned | H |

TABLE 3-continued

Markers associated with detection of Polled in Hereford

| | | |
|---|---|---|
| GCAGT | Horned | H |
| GCTGG | Horned | H |
| GCTGT | Polled | P |
| GTTAT | Polled | P |
| GTTGG | Polled | P |
| GTTGT | Inconsistent | I |

TABLE 4

28 Nucleotide-marker haplotypes associated with detection of Polled in Angus and Red Angus. Markers are ordered according to their positions in Btau3.0: 1013610-1352705-1352905-1356048-1431709-1438531-1731905-1872077-1872200-2101528-2128551-2214142-2220054-2220178-2225310-2288436-2332892-2333140-2338338-2640799-2648129-2650867-2651006-2657651-2676311-2816109-2816370-2820224

| SEQ ID NO: | Haplotype | N |
|---|---|---|
| 80 | GTCGGTAATTCACATGCATATTGGCTCT | 8 |
| 81 | GTCGGTAATTCACATGCGCATTGGCTCT | 22 |
| 82 | GTCGGTAATTTTTTCGTGCATTGGCTCT | 2 |
| 83 | GTCAGTAATTCTTTCGCACATTGGCTCT | 20 |
| 84 | GTCAGTAATTCTTTCGCACATTGGCGGT | 1 |
| 85 | GTCAGTAATTCTTTCGCACATAGCCTCT | 2 |
| 86 | GTCAGTAATTCTTTCACACATTGGCTCT | 1 |
| 87 | GTCAGTAATCTTTTCGCGCATTGGCTCT | 15 |
| 88 | GTCAGTAGTTCACTCGTACATTGGCTGT | 1 |
| 89 | GAGAGTAATTCTTTCACACATTGGCTCT | 2 |
| 90 | GAGAGTAATTCTTTCACACATAGCCTCT | 5 |
| 91 | GAGAGTAATTTTTTCACATATAGCCTCT | 9 |
| 92 | CTCGGTAATTCTTTCGCACATTGGCTCT | 7 |
| 93 | CTCGGTAATTCTTTCACACATTGGCTCT | 1 |
| 94 | CTCGGTAATTCTTTCACACATAGCCTCT | 11 |
| 95 | CTCAGTAATTCTTTCGCACATTGGCTCT | 2 |
| 96 | CAGAGTAATTTTTTCACATATAGCCTCT | 3 |

TABLE 5

Observed eight-marker haplotypes to distinguish horned and polled in Gelbvieh. Markers are ordered according to their positions in Btau3.0: 1356048-2128551-2220054-2288436-2332892-2333140-2650867-2816109

| Haplotype | Assoc Phenotype |
|---|---|
| ACTACAAT | Polled |
| ACTGCATT | Polled |
| ACTGCGAT | Horned |
| ACTGCGTT | Horned |
| ATTACAAT | Polled |
| ATTACGAT | Horned |
| ATTATGAT | Horned |
| ATTATGTT | Horned |
| ATTGCAAT | Polled |
| ATTGCATT | Polled |
| ATTGCGAT | Horned |
| ATTGCGTT | Polled |
| GCCGCATT | Polled |
| GCCGCGTG | Polled |
| GCCGCGTT | Polled |
| GCTACAAT | Polled |
| GCTGCGAT | Horned |
| GCTGCGTT | Horned |
| GTTACGTT | Polled |
| GTTGCATT | Horned |
| GTTGCGTG | Horned |

TABLE 6

Observed six nucleotide-marker haplotypes to distinguish horned and polled in Charolais. Markers are ordered according to their positions in Btau3.0: 1013610-1731905-1872077-2214142-2332892-2816109

| Haplotype | Assoc. Phenotype | N |
|---|---|---|
| CAAATG | horned | 2 |
| CAATCT | horned | 2 |
| CAATTT | horned | 7 |
| GAAACG | horned | 2 |
| GAAACT | horned | 2 |
| GAAATG | horned | 4 |
| GAATCT | polled | 57 |
| GAGATT | horned | 1 |
| GAGTCT | horned | 1 |
| GAGTTG | horned | 4 |
| GAGTTT | horned | 14 |
| GGATCT | horned | 1 |
| GGATTG | horned | 1 |

TABLE 7

Observed eight-marker haplotypes to distinguish horned and polled in Shorthorn. Markers are ordered according to their positions in Btau3.0: 1731905-2101528-2128551-2214142-2288436-2332892-2333140-2816109.

| Haplotype | Assoc. Phenotype | N |
|---|---|---|
| ACTAGCGG | horn | 1 |
| ACTAGTGT | horn | 1 |
| ACTTACGT | horn | 3 |
| ATCTATGT | horn | 12 |
| ATTTACGT | horn | 2 |
| ATTTATGT | horn | 1 |
| ATTTGCAT | horn | 4 |
| ATTTGCAT | horn | 1 |
| ATTTGTGT | horn | 11 |
| ATTTGTGT | horn | 1 |
| GCTTGCGG | horn | 3 |
| GTTAGCGT | horn | 2 |
| ACTTACAT | horn | 2 |
| GCTTGCGT | horn | 1 |
| ATCTGCAT | inconsistent | 3 |
| ACTTGCGG | poll | 6 |
| ACTTGCGT | poll | 8 |
| ATTTACAT | poll | 20 |

TABLE 8

Observed four-marker haplotypes to distinguish horned and polled in Jersey. Markers are ordered according to their positions in Btau3.0: 1356048-2101528-2288436-2333140.

| Haplotype | Assoc. Phenotype | N |
|---|---|---|
| ACGG | horned | 9 |
| ACGG | horned | 1 |
| ACGG | horned | 1 |
| ACGG | horned | 14 |
| ATGG | horned | 2 |
| GCGG | horned | 2 |
| GTAA | polled | 1 |
| GTAG | polled | 2 |
| GTAA | polled | 12 |
| ATAG | horned | 4 |

TABLE 9

Observed six marker haplotypes to distinguish horned and polled in Holstein. Markers are ordered according to their positions in Btau3.0: 1352705-1356048-1731905-1872077-2288436-2640799

| Haplotype | Assoc. Phenotype |
|---|---|
| AAAGAA | horn |
| AAAGAT | poll |
| AAAGGA | horn |
| AAGAAA | horn |
| AAGAGA | horn |
| AGAAAA | horn |
| TAAAAA | horn |
| TAAAAT | poll |
| TAAAGA | horn |
| TAAGAA | horn |

TABLE 9-continued

Observed six marker haplotypes to distinguish horned and polled in Holstein. Markers are ordered according to their positions in Btau3.0: 1352705-1356048-1731905-1872077-2288436-2640799

| Haplotype | Assoc. Phenotype |
|---|---|
| TAGAAA | horn |
| TAGAGA | horn |
| TGAAAA | poll |
| TGAAAT | poll |
| TGAAGA | horn |
| TGAGAA | horn |
| TGGAAT | poll |

TABLE 10

Observed ten-marker haplotypes to distinguish horned and polled in Simmental. Markers are ordered according to their positions in Btau3.0: 1356048-1731905-1872077-1872200-2101528-2214142-2288436-2332892-2333140-650867.

| SEQ ID NO: | Haplotype | Assoc. Phenotype | N |
|---|---|---|---|
| 97 | AAATCTGCGT | poll | 29 |
| 98 | AAATTTGCAT | poll | 13 |
| 99 | AAGCTTATGT | horn | 13 |
| 100 | GAATTTACGT | horn | 11 |
| 101 | AAATTTATGT | horn | 10 |
| 102 | AAATTAGCGT | poll | 8 |
| 103 | GAATTAGCGT | poll | 8 |
| 104 | AGATTTATGT | horn | 6 |
| 105 | GAATTTGCGT | horn | 6 |
| 106 | GAGCTTATGT | horn | 6 |
| 107 | AAATTTACAA | poll | 5 |
| 108 | GAATCTGCGT | poll | 4 |
| 109 | AAATTTGTGT | horn | 3 |
| 110 | AAGCTTACAT | horn | 3 |
| 111 | GAATTTGCAT | horn | 3 |
| 112 | GAATTTGCGA | horn | 3 |
| 113 | AAATTTACAT | inconsistent | 2 |
| 114 | AAATTTGCGT | poll | 2 |
| 115 | AAGCTTGCGT | horn | 2 |
| 116 | AGATTTGCGT | horn | 2 |
| 117 | AGGCTAATAT | poll | 2 |

TABLE 10-continued

Observed ten-marker haplotypes to distinguish horned and polled in Simmental. Markers are ordered according to their positions in Btau3.0: 1356048-1731905-1872077-1872200-2101528-2214142-2288436-2332892-2333140-650867.

| SEQ ID NO: | Haplotype | Assoc. Phenotype | N |
|---|---|---|---|
| 118 | GAATTTATGT | horn | 2 |
| 119 | AAATCTACAT | horn | 1 |
| 120 | AAGCTTGCAT | poll | 1 |
| 121 | AAGTTAGCGT | poll | 1 |
| 122 | AGATTTGTGT | horn | 1 |
| 123 | GAATTAACAT | poll | 1 |
| 124 | GAATTTGTGT | horn | 1 |
| 125 | GGATCTACGT | poll | 1 |

Example 5

FIG. 48 shows a flowchart of the input of data and the output of results from the analysis and correlation of the data pertaining to the breeding, veterinarian histories and performance requirements of a group of animals such as from bovines. The flowchart illustrated in FIG. 48 further indicates the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 49:
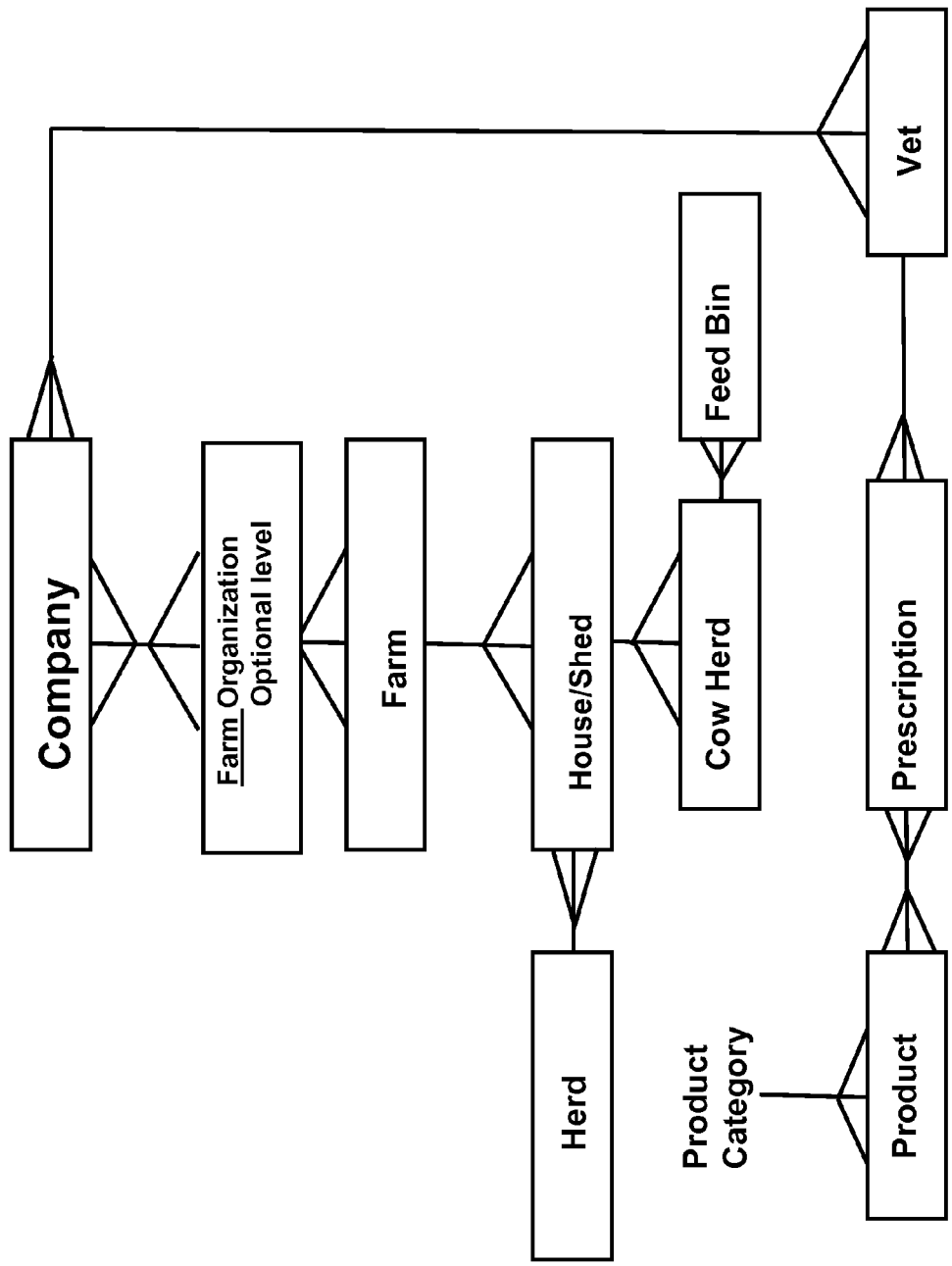
FIG. 49 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 49 illustrates potential relationships between the data elements to be entered into the system. Unidirectional arrows indicate, for example, that a house or shed is typically owned by only one farm, whereas a farm may own several houses or sheds. Similarly, a prescription may include have several veterinarian products.

Figure 50A:
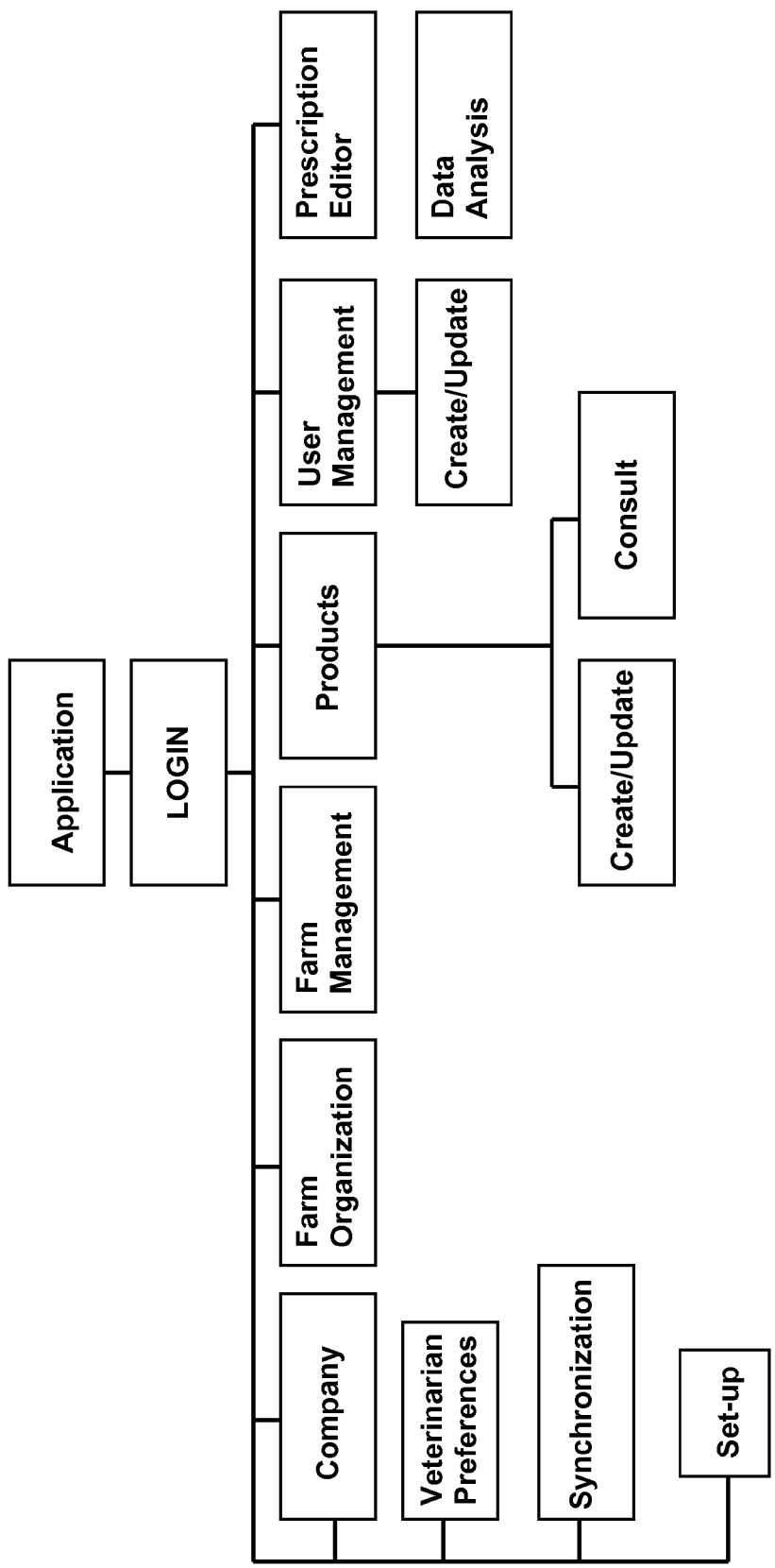
FIG. 50A illustrates the flow of events in the use of the portable computer-based system for data entry on the breeding and rearing of a herd of cows.
Figure 50B:
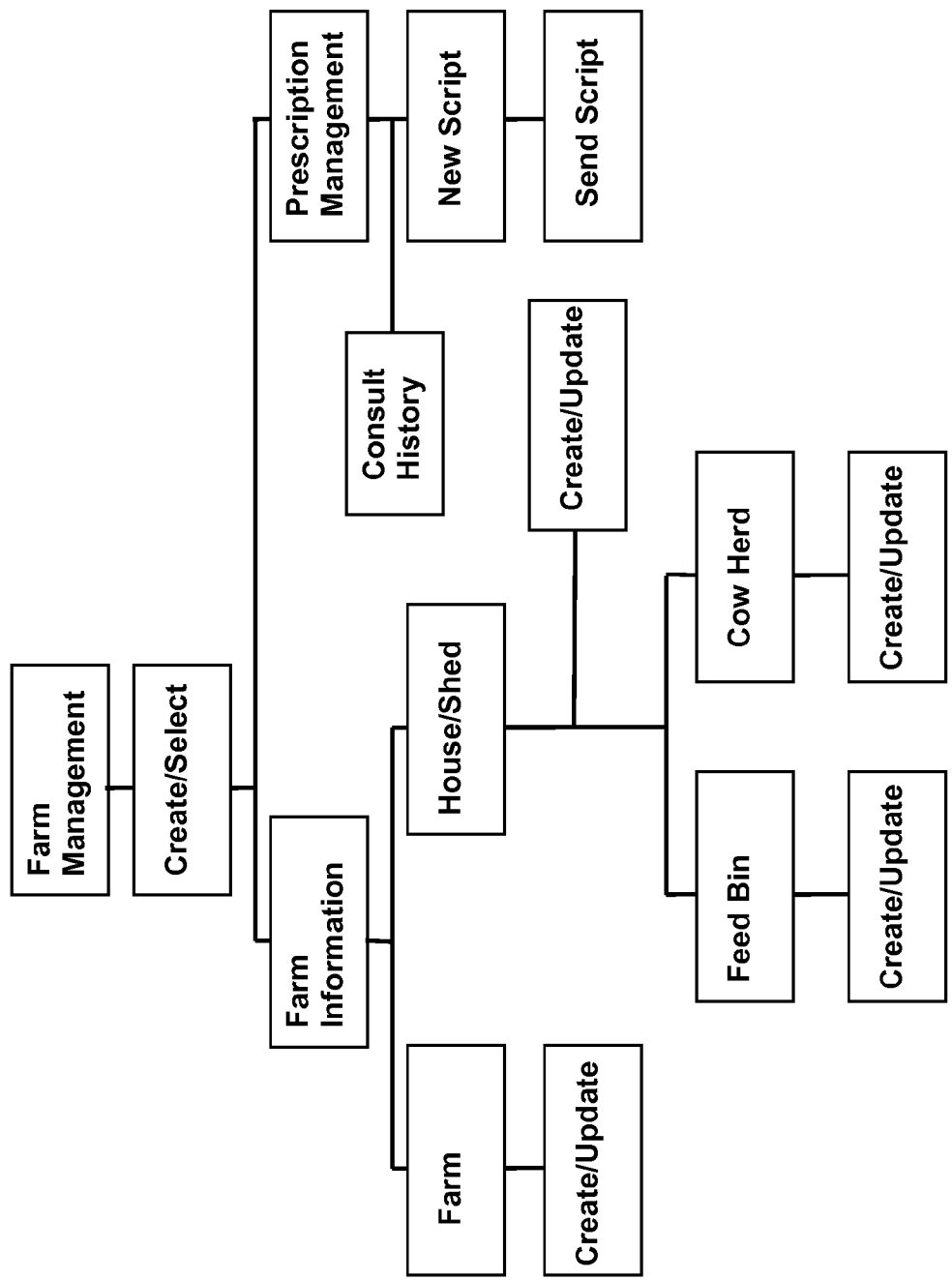
FIG. 50B illustrates the flow of events through the subroutines related to data entry concerning farm management.

FIG. 50A illustrates the flow of events in the use of the portable computer-based system for data entry on the breeding and rearing of a herd of cows. FIG. 50B illustrates the flow of events through the sub-routines related to data entry concerning farm management. FIG. 50C illustrates the flow of events through the sub-routines related to data entry concerning data specific to a company.

Figure 51:
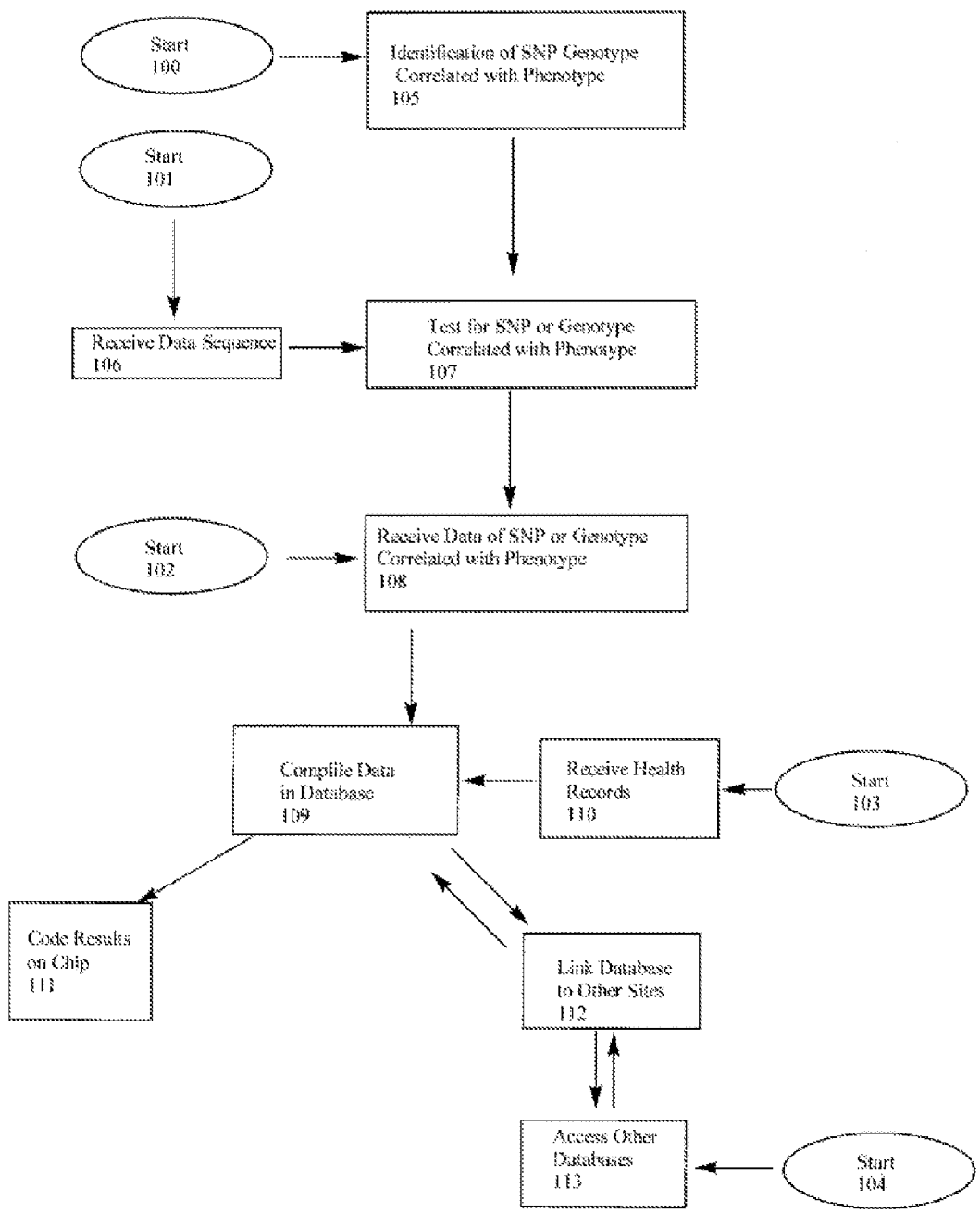
FIG. 51 illustrates a flow chart of the input of data and the output of results from the analysis and the correlation of the data pertaining to the breeding, veterinarian histories, and performance requirements of a group of animals.

FIG. 51 illustrates a flow chart of the input of data and the output of results from the analysis and correlation of the data pertaining to the breeding, veterinarian histories, and performance requirements of a group of animals.

The invention is further described by the following numbered paragraphs:

1. A method for sub-grouping animals according to genotype wherein the animals of each sub-group have similar polymorphism in Polled-associated gene(s) comprising:
(a) determining the genotype of each animal to be sub-grouped by determining the presence of single nucleotide polymorphisms in or near the Polled gene(s), and
(b) segregating individual animals into sub-groups wherein each animal in a sub-group has similar polymorphisms in the Polled gene(s).

2. A method for sub-grouping animals according to genotype wherein the animals of each sub-group have similar genotypes in the Polled gene(s) comprising:

(a) determining the genotype of each animal to be sub-grouped by determining the presence of single nucleotide polymorphisms of interest in or near the Polled gene(s), (b) segregating individual animals into sub-groups depending on whether the animals have, or do not have, the single nucleotide polymorphism(s) of interest in or near the Polled gene(s).

3. The method of paragraphs 1 or 2, wherein the single nucleotide polymorphism(s) of interest is selected from the group, wherein the single nucleotide polymorphism(s) of interest is selected from the group consisting of the nucleotide substitutions defined in SEQ ID NO 1 through SEQ ID NO 42 (FIG. 1 through FIG. 42).

4. A method for sub-grouping animals according to genotype wherein the animals of each sub-group have a similar genotype in the Polled gene(s) comprising:

(a) determining the genotype of each animal to be sub-grouped by determining the presence of a nucleotide substitutions defined in SEQ ID NO 1 through SEQ ID NO 42 (FIG. 1 through FIG. 42).

(b) segregating individual animals into sub-groups depending on whether the animals have, or do not have nucleotide substitution(s) defined as defined in SEQ ID NO 1 through SEQ ID NO 42 (FIG. 1 through FIG. 42).

5. A method for identifying an animal having a desirable phenotype as compared to the general population of animals of that breed, comprising determining the presence of a single nucleotide polymorphism(s) in the Polled gene(s) of the animal, wherein the polymorphism is selected from the group comprising the nucleotide substitutions defined in SEQ ID NO 1 through SEQ ID NO 42 (FIG. 1 through FIG. 42)

6. The method of any one of paragraphs 1 to 5 wherein the animal is a bovine.

7. The method of any one of paragraphs 1 to 6 wherein the Polled gene(s) are bovine Polled gene(s).

8. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

9. The method according to paragraph 8, wherein the computer system is an interactive system whereby modifications to the output of the computer-assisted method may be correlated according to the input from the interactive device.

10. The method according to paragraph 8 or 9, further comprising the steps of inputting into the programmed computer diagnostic data related to the health of the cow or herd of cows; and correlating the diagnostic data to the breeding and veterinary histories of the cow or herd of cows.

11. The method according to any one of paragraphs 8 to 10, wherein the veterinary data comprise a vaccination record for a cow or herd of cows.

12. The method according to any one of paragraphs 8 to 11 wherein the health data are selected from the group consisting of husbandry condition data, herd history, and food safety data.

13. The method according to any one of paragraphs 8 to 12, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

14. The method according to any one of paragraphs 8 to 13, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines thereby improving bovine production.

15. The computer-assisted method according to any one of paragraphs 8 to 14 for optimizing efficiency of feedlots for livestock comprising outputting to the output device the breeding and veterinary history of the bovine or herd of bovines, thereby optimizing efficiency for the bovine or herd of bovines.

16. A method of transmitting data comprising transmission of information from such methods according to any one of paragraphs 8 to 14, selected from the group consisting of telecommunication, telephone, video conference, mass communication, a presentation, a computer presentation, a POWERPOINT™ presentation, internet, email, and documentary communication.

17. An interactive computer system according to any one of paragraphs 8 to 14 for tracking breeding and welfare histories of cows comprising breeding and veterinarian data corresponding to a bovine or herd of bovines, and wherein the computer system is configured to allow the operator thereof to exchange data with the device or a remote database.

18. The interactive computer system according to paragraph 19, wherein the input and output devices are a personal digital assistant or a pocket computer.

19. A method of doing business for tracking breeding and welfare histories of livestock comprising breeding and veterinarian data corresponding to one or more livestock animals comprising providing to a user the computer system of paragraph 17.

20. A method of doing business for tracking breeding and welfare histories of livestock comprising breeding and veterinarian data corresponding to one or more livestock animals comprising providing to a user the computer system of paragraph 18.

21. The method of doing business according to paragraph 19, further comprising providing the animal owner or customer with sample collection equipment, such as swabs and tags useful for collecting samples from which genetic data may be obtained, and wherein the tags are optionally packaged in a container which is encoded with identifying indicia.

22. The method of doing business according any one of paragraphs 8 to 14, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

23. The method of any one of paragraphs 6 to 22 wherein the data comprises presence or absence of one or more of a single nucleotide polymorphism(s) of interest in the Polled gene(s).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08105776B2). An electronic copy of the "Sequence Listing" will also be available from the USPTO upon request and payment of the fee set forth in 37 CFR 1.19(b)(3).

What is claimed is:

1. A method for identifying a bovine animal having Polled phenotype, as compared to a general population of bovine animals, comprising:
    (a) obtaining a biological sample from said bovine animal;
    (b) subjecting the sample to nucleotide sequence analysis to obtain sufficient nucleotide sequence information to provide the identity of the nucleotides at positions corresponding to the following SEQ ID NO: 43 positions: 1356048, 1872077, 1872200, 2101528, 2214142, 2220054, 2220178, 2225310, 2288436, 2332892, 2333140, 2338338, 2816109, 2816370, 1013610, 1352705, 1352905, 1431709, 1438531, 1731905, 2128551, 2640799, 2648129, 2650867, 2651006, 2657651, 2676311, and 2820224;
    (c) detecting in said animal a haplotype of the alleles present at at least three nucleotides or a genotype of the alleles present at at least five nucleotides, wherein the at least three or at least five nucleotides in the haplotype or the genotype are nucleotides detected at the positions analyzed in part (b), wherein said haplotype or said genotype is sufficient to conclude that the animal will exhibit the Polled phenotype;
    (d) identifying the animal as having the Polled phenotype based on the presence the haplotype comprised of at least three of said positions or the genotype comprised of at least five positions.

2. The method of claim 1 wherein:
    (a) the animal is of the Limousin breed and a three SNP haplotype is detected;
    (b) the animal is of the Hereford breed and a five SNP haplotype is detected;
    (c) the animal is of the Shorthorn breed and an eight SNP haplotype is detected;
    (d) the animal is of the Charolais breed and a six SNP haplotype is detected;
    (e) the animal is of the Jersey breed and a four SNP haplotype is detected; or
    (f) the animal is of the Gelbvieh breed and an eight SNP haplotype is detected.

3. The method of claim 2, wherein the three SNP haplotype consists of alleles present at nucleotide positions 1872077, 2288436, and 2332892.

4. The method of claim 2, wherein the five SNP haplotype consists of alleles present at nucleotide positions 1356048, 2101528, 2214142, 2333140, and 2816109.

5. The method of claim 2, wherein the eight SNP haplotype for the Galbvieh breed consists of alleles present at nucleotide positions 1356048, 2220054, 2288436, 2332892, 2333240, 2816109, 2128551, and 2650867.

6. The method of claim 2, wherein the six SNP haplotype consists of alleles present at nucleotide positions 1872077, 2214142, 2332892, 2816109, 1013610, and 1731905.

7. The method of claim 2, wherein the eight SNP haplotype for the Shorthorn breed consists of alleles present at nucleotide positions 2101528, 2128551, 2214142, 2288436, 2332892, 2333140, 2816109 and 1731905.

8. The method of claim 2, wherein the four SNP haplotype consists of alleles present at nucleotide positions 1256048, 2101528, 2288436, and 233140.

9. A method of sub-grouping bovine animals comprising
    (a) identifying bovine animals having the Polled phenotype using the method set forth in claim 1 or claim 2, and
    (b) sub-grouping the animals according to the haplotype or genotype that was detected.

* * * * *

UNITED STATES PATENT AND TRADEMARK OFFICE
CERTIFICATE OF CORRECTION

PATENT NO. : 8,105,776 B2  
APPLICATION NO. : 12/338835  
DATED : January 31, 2012  
INVENTOR(S) : Clare A. Gill et al.

Page 1 of 1

It is certified that error appears in the above-identified patent and that said Letters Patent is hereby corrected as shown below:

Column 48, line 42, (claim 5), "2333240" should be --2333140--

Column 48, line 52, (claim 8), "1256048" should be --1356048--

Signed and Sealed this
Sixteenth Day of October, 2012

David J. Kappos
*Director of the United States Patent and Trademark Office*